US010299500B2

(12) United States Patent
Passe et al.

(10) Patent No.: US 10,299,500 B2
(45) Date of Patent: May 28, 2019

(54) GRANULES OF PROTEIN-RICH MICROALGAL BIOMASS FLOUR AND METHOD FOR PREPARING SAME

(71) Applicant: Corbion Biotech, Inc., South San Francisco, CA (US)

(72) Inventors: Damien Passe, Douai (FR); Francois Delannoy, Lestrem (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 402 days.

(21) Appl. No.: 15/039,868

(22) PCT Filed: Nov. 27, 2014

(86) PCT No.: PCT/FR2014/053052
§ 371 (c)(1),
(2) Date: May 27, 2016

(87) PCT Pub. No.: WO2015/079169
PCT Pub. Date: Jun. 4, 2015

(65) Prior Publication Data
US 2016/0374379 A1 Dec. 29, 2016

(30) Foreign Application Priority Data

Nov. 29, 2013 (FR) ...................................... 13 61877
Jun. 27, 2014 (FR) ...................................... 14 56034

(51) Int. Cl.
| A23L 17/60 | (2016.01) |
| A23K 10/30 | (2016.01) |
| A23L 27/60 | (2016.01) |
| A21D 13/80 | (2017.01) |
| A23L 23/00 | (2016.01) |
| A61K 8/9706 | (2017.01) |
| A61K 9/00 | (2006.01) |
| A61K 9/20 | (2006.01) |
| A61K 36/05 | (2006.01) |
| A61K 47/46 | (2006.01) |
| A61Q 19/00 | (2006.01) |
| A23K 50/42 | (2016.01) |

(52) U.S. Cl.
CPC .............. *A23L 17/60* (2016.08); *A21D 13/80* (2017.01); *A23K 10/30* (2016.05); *A23K 50/42* (2016.05); *A23L 23/00* (2016.08); *A23L 27/60* (2016.08); *A23L 27/63* (2016.08); *A61K 8/9706* (2017.08); *A61K 9/0056* (2013.01); *A61K 9/2068* (2013.01); *A61K 36/05* (2013.01); *A61K 47/46* (2013.01); *A61Q 19/00* (2013.01); *A23V 2002/00* (2013.01); *A61K 2236/00* (2013.01); *A61K 2800/10* (2013.01); *A61K 2800/85* (2013.01)

(58) Field of Classification Search
None
See application file for complete search history.

(56) References Cited

U.S. PATENT DOCUMENTS

| 3,962,466 | A | 6/1976 | Nakabayashi |
| 4,564,526 | A | 1/1986 | Takashima |
| 4,917,915 | A | 4/1990 | Cain et al. |
| 4,978,553 | A | 12/1990 | Silver |
| 5,346,716 | A | 9/1994 | Bakal et al. |
| 5,487,916 | A | 1/1996 | Christensen |
| 5,512,311 | A | 4/1996 | Capitani et al. |
| 5,547,699 | A | 8/1996 | Iizuka et al. |
| 5,693,357 | A | 12/1997 | Wong et al. |
| 5,792,631 | A | 8/1998 | Running |
| 6,255,505 | B1 | 7/2001 | Bijl et al. |
| 6,372,460 | B1 | 4/2002 | Gladue et al. |
| 6,607,900 | B2 | 8/2003 | Bailey et al. |
| 8,709,750 | B2 | 4/2014 | Gordon et al. |
| 2002/0068110 | A1 | 6/2002 | Liu et al. |
| 2007/0099280 | A1 | 5/2007 | Barclay |
| 2009/0286295 | A1 | 11/2009 | Medoff et al. |
| 2010/0297295 | A1 | 11/2010 | Brooks et al. |
| 2010/0297296 | A1 | 11/2010 | Brooks et al. |
| 2010/0297323 | A1 | 11/2010 | Brooks et al. |
| 2010/0297325 | A1 | 11/2010 | Brooks et al. |

(Continued)

FOREIGN PATENT DOCUMENTS

| CN | 1596694 | 3/2005 |
| CN | 102643714 A | 8/2012 |

(Continued)

OTHER PUBLICATIONS

Monica Fradique et al.: "Incorporation of Chlorella vulgaris and Spirulina maxima biomass in pasta products. Part 1: Preparation and evaluation", Journal of the Science of Food and Agriculture, vol. 90, No. 10, Aug. 15, 2010 (Aug. 15, 2010), pp. 1656-1664, XP055027243.

Nalin Samarasinghe et al.: "Algal cell rupture using high pressure homogenization as a prelude to oil extraction", Renewable Energy, Pergamon Press, Oxford, GB, vol. 48, Apr. 20, 2012 (Apr. 20, 2012), pp. 300-308, XP028428119, ISSN: 0960-1481, DOI: 10.1016/J.RENENE.2012.04.039 [retrieved on May 11, 2012] p. 301-p. 302.

Spiden Erin M et al.: "Quantitative evaluation of the ease of rupture of industrially promising microalgae by high pressure homogenization", Bioresource Technology, Elsevier BV, GB, vol. 140, Apr. 28, 2013 (Apr. 28, 2013), pp. 165-171, XP028565382, ISSN: 0960-8524, DOI: 10.1016/J.BIORTECH.2013.04.074 the whole document.

(Continued)

*Primary Examiner* — Michael Barker
(74) *Attorney, Agent, or Firm* — Weaver Austin Villeneuve & Sampson LLP

(57) ABSTRACT

Granules of protein-rich microalgal biomass flour having: a particle size distribution, measured on an LS laser granulometer of the COULTER® brand, with a Dmode of 60 to 300 μm and a D4.3 of 70 to 420 μm; an aerated density, measured on a HOSOKAWA Powder Characteristics Tester, of 0.60 to 0.70 g/mL, and a compressibility, measured on a HOSOKAWA Powder Characteristics Tester, of 15 to 25%.

21 Claims, No Drawings

(56) References Cited

U.S. PATENT DOCUMENTS

| | | |
|---|---|---|
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1* | 12/2010 | Brooks .................. A21D 2/165 426/541 |
| 2010/0303990 A1 | 12/2010 | Brooks et al. |
| 2011/0256282 A1 | 10/2011 | Piechocki et al. |
| 2011/0305740 A1 | 12/2011 | Boursier et al. |
| 2011/0311599 A1 | 12/2011 | Boursier et al. |
| 2013/0122180 A1 | 5/2013 | Brooks et al. |
| 2014/0106051 A1 | 4/2014 | Lefevre et al. |
| 2015/0272136 A1* | 10/2015 | Guillemant ............... A23L 3/46 426/550 |
| 2016/0015071 A1 | 1/2016 | Delebarre et al. |
| 2016/0021893 A1 | 1/2016 | Delebarre et al. |
| 2016/0021895 A1 | 1/2016 | Leroux et al. |
| 2016/0029684 A1 | 2/2016 | Passe |
| 2016/0143337 A1 | 5/2016 | Passe |
| 2016/0324167 A1 | 11/2016 | Brooks et al. |
| 2018/0139994 A1 | 5/2018 | Brooks et al. |
| 2018/0213831 A1 | 8/2018 | Delebarre |
| 2018/0228188 A1 | 8/2018 | Delebarre et al. |

FOREIGN PATENT DOCUMENTS

| | | |
|---|---|---|
| DE | 10 2006 056454 A1 | 5/2008 |
| EP | 0 622 027 A2 | 11/1994 |
| EP | 1 853 124 B1 | 9/2008 |
| EP | 2 183 977 A1 | 5/2010 |
| FR | 2 924 126 A1 | 5/2009 |
| JP | 360075244 | 10/1983 |
| JP | 409252707 A | 9/1997 |
| JP | 2012-505656 | 3/2012 |
| JP | 2012-519011 | 8/2012 |
| JP | 2012-519013 | 8/2012 |
| JP | 2012-523843 | 10/2012 |
| WO | WO 98/09700 | 3/1998 |
| WO | WO 2001/44440 | 6/2001 |
| WO | WO 2006/122299 | 11/2006 |
| WO | WO 2010/045368 | 4/2010 |
| WO | WO 2010/100368 | 9/2010 |
| WO | WO 2010/100369 | 9/2010 |
| WO | WO 2010/120923 | 10/2010 |
| WO | WO 2011/108919 | 9/2011 |
| WO | WO 2011/130578 | 10/2011 |
| WO | WO 2011/150411 | 12/2011 |
| WO | WO 2012/095121 A1 | 7/2012 |
| WO | WO 2013/059023 | 4/2013 |
| WO | 2014/062882 A1 | 4/2014 |
| WO | WO 2014/064231 | 5/2014 |
| WO | WO 2014/140242 | 9/2014 |
| WO | WO 2014/140244 | 9/2014 |
| WO | WO 2014/140245 | 9/2014 |
| WO | WO 2014/140247 | 9/2014 |
| WO | WO 2015/079169 | 6/2015 |

OTHER PUBLICATIONS

Becker et al: "Micro-algae as a source of protein", Biotechnology Advances, Elsevier Publishing, Barking, GB, vol. 25, No. 2, Jan. 26, 2007 (Jan. 26, 2007), pp. 207-210, XP005862318, ISSN: 0734-9750, DOI: 10.1016/J.BIOTECHADV.2006.11.002 the whole document.
International Search Report, dated Feb. 16, 2015, from corresponding PCT application.
U.S. Appl. No. 14/056,100, Request for Restriction Requirement, dated Sep. 21, 2016.
U.S. Appl. No. 14/056,100, Non-Final Office Action, dated Apr. 4, 2017.
Restriction Requirement, dated Apr. 10, 2017, in U.S. Appl. No. 14/438,239.
Non-Final Rejection, dated Jan. 12, 2018, in U.S. Appl. No. 14/438,239.
Restriction Requirement, dated Sep. 5, 2017, in U.S. Appl. No. 14/776,751.
Non-Final Rejection, dated Apr. 2, 2018, in U.S. Appl. No. 14/776,751.
Non-Final Rejection, dated Apr. 28, 2017, in U.S. Appl. No. 14/776,930.
Final Rejection, dated Aug. 21, 2017, in U.S. Appl. No. 14/776,930.
Non-Final Rejection, dated Dec. 21, 2017, in U.S. Appl. No. 14/776,930.
Final Rejection, dated Jun. 20, 2018, in U.S. Appl. No. 14/776,930.
Non-Final Rejection, dated Sep. 15, 2017, in U.S. Appl. No. 14/776,962.
Non-Final Rejection, dated Dec. 9, 2016, in U.S. Appl. No. 14/776,962.
Final Rejection, dated Nov. 17, 2017, in U.S. Appl. No. 14/776,962.
Final Rejection, dated May 1, 2017, in U.S. Appl. No. 14/776,962.
Restriction Requirement, dated May 30, 2017, in U.S. Appl. No. 14/776,949.
Non-Final Rejection, dated Jul. 10, 2017, in U.S. Appl. No. 14/776,949.
Restriction Requirement, dated Oct. 4, 2017, in U.S. Appl. No. 14/905,342.
Restriction Requirement, dated Mar. 9, 2018, in U.S. Appl. No. 14/905,342.
Non-Final Office Action, dated Jul. 2, 2018, in U.S. Appl. No. 14/905,342.
Final Rejection, dated Oct. 31, 2017, in U.S. Appl. No. 14/776,949.
Non-Final Rejection, dated Jun. 15, 2018, in U.S. Appl. No. 15/955,468.
Final Rejection, dated Oct. 10, 2018, in U.S. Appl. No. 14/438,239.
Final Rejection, dated Sep. 26, 2018, in U.S. Appl. No. 14/045,100.
Non-Final Rejection, dated Nov. 29, 2018, in U.S. Appl. No. 14/776,930.
Final Rejection, dated Dec. 5, 2018, in U.S. Appl. No. 15/955,468.
International Search Report, dated Feb. 6, 2014, for International Application No. PCT/EP2013/072343, pp. 1-8.
Written Opinion in International Application No. PCT/EP2013/072343, dated Feb. 6, 2014, pp. 1-8.
International Search Report, dated May 27, 2014, for International Application No. PCT/EP2014/055057, pp. 1-8.
Written Opinion in International Application No. PCT/EP2014/055057, dated May 27, 2014, pp. 1-8.
International Search Report, dated May 30, 2014, for International Application No. PCT/EP2014/055063, pp. 1-8 and English Translation.
Written Opinion in International Application No. PCT/EP2014/055063, dated May 30, 2014, pp. 1-8 and English Translation.
International Search Report, dated Jun. 16, 2014, from International Application No. PCT/EP2014/055060, pp. 1-8 and English Translation.
Written Opinion in International Application No. PCT/EP2014/055060, dated Jun. 16, 2014, pp. 1-8 and English Translation.
International Search Report, dated Jun. 16, 2014, from International Application No. PCT/EP2014/055061, pp. 1-9 and English Translation.
Written Opinion in International Application No. PCT/EP2014/055061, dated Jun. 16, 2014, pp. 1-9 and English Translation.
International Search Report, dated Feb. 4, 2015, from International Patent Application No. PCT/FR14/051841, filed Jul. 17, 2014 and English Translation.
Written Opinion, dated Feb. 4, 2015, from International Patent Application No. PCT/FR14/051841, filed Jul. 17, 2014 and English Translation.
Written Opinion, dated Feb. 16, 2015, from corresponding PCT application, (International Patent Application No. PCT/FR14/53052, filed Nov. 27, 2014) and English Translation.
Australian Patent Application No. 2013331243, Patent Examination Report No. 1, dated May 30, 2016.
Australian Patent Application No. 2013331243, Patent Examination Report No. 2, dated Feb. 8, 2017.
Australian Patent Application No. 2013331243, Patent Examination Report No. 3, dated May 4, 2017.
Chinese Patent Application No. 201380054255.X, Notification of First Office Action, dated Nov. 28, 2016.
Chinese Patent Application No. 201380054255.X, Notification of Second Office Action, dated Aug. 8, 2017.

(56) References Cited

OTHER PUBLICATIONS

Chinese Patent Application No. 201380054255.X, Notification of Third Office Action, dated Feb. 1, 2018.
Supplemental European Search Report, dated Apr. 25, 2016, for European Patent Application No. 13 84 7337.
Extended European Search Report, dated May 3, 3016, including the Supplemental European Examination Report, dated Apr. 25, 2016, for European Patent Application No. 13 84 7337.
Examination Report, dated Nov. 30, 2017, for European Patent Application No. 13 84 7337.
International Search Report, dated Feb. 21, 2014, for International Patent Application No. PCT/US2013/65369.
Written Opinion of the International Searching Authority, dated Feb. 21, 2014, for International Patent Application No. PCT/US2013/65369.
International Preliminary Examination Report, dated Apr. 21, 2015, for International Patent Application No. PCT/US2013/65369.
Notice for Reasons for Rejection, dated Aug. 31, 2017, for Japanese Patent Application No. 2015-537812, with English Translation.
Notice for Reasons for Rejection, dated Mar. 30, 2018, for Japanese Patent Application No. 2015-537812, with English Translation.
Notice for Reasons for Rejection, dated Apr. 18, 2018, for Japanese Patent Application No. 2017-128829 (in Japanese).
First Examination Report, dated Feb. 7, 2018, for New Zealand Patent Application No. 707192.
Japanese Patent Application No. JP 2015-562181, 1st Notice of Reasons for Rejection, dated Oct. 4, 2017, No Translation.
Japanese Patent Application No. JP 2015-562181, 2nd Notice of Reasons for Rejection, dated Jun. 14, 2018, with English Translation.
Chinese Patent Application No. 201480014074.9, Decision of Rejection, dated Jan. 15, 2018, with English translation.
European Patent Application No. EP 14 711 947.3, Office Action, dated Dec. 5, 2017. (in French).
Japanese Patent Application No. JP 2015-562178, Notice of Reasons for Rejection, dated Nov. 22, 2018, with English translation.
Further Examination Report, dated Aug. 8, 2018, for New Zealand Patent Application No. 707192.
Communication pursuant to Article 94(3) EPC, dated Aug. 14, 2018, for Europrean Patent Application No. 13 847 337.
Chinese Patent Application No. 201380054255.X, Rejection Decision, dated Aug. 28, 2018.
Australian Patent Application No. 2017225129, Patent Examination Report No. 1, dated Aug. 13, 2018.
Notice for Reasons for Rejection, dated Nov. 9, 2018, for Japanese Patent Application No. 2017-128829 (in Japanese).
Further Examination Report, dated Nov. 12, 2018, for New Zealand Patent Application No. 707192.
"BETE Spray Dry Manual", BETE Fog Nozzle, 2005, p. 1-25 (Year: 2005).
"Solazyme Roquette Nutritionals Golden Chlorella® Omega to be key ingredient in Natural Vitality Release of new 30oz Bottle for Energy28", (Mar 10, 2011), http://investors.terravia.com/releasedetail.cfm?releaseid=588870.
Batista, A.P., et al., "Microalgae bioactive components for innovative food products development," 37th WEFTA Meeting Book of Abstracts, INRB/IPIMAR, Abstract S3.14, p. 134, (2007).
Belasco, Warren, "Algae Burgers for a Hungry World? The Rise and Fall of Chlorella Cuisine," Technology and Culture, 38(3):608-634, (1997).
Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.
Database WPI, AN 1978-43554A, Week 1978, XP002724795, Thomson Scientific, London, Great Britain, Aug. 5, 1977, p. 1.
Database WPI, AN 2005-480030, Week 200549, XP002694315, Thomson Scientific, London, Great Britain, Mar. 23, 2015, p. 1.
Database WPI, AN 2013-e 16999, Week 2013, XP002725042, Thomson Scientific, London, Great Britain, Apr. 9, 2012, p. 1.
Fradique et al., "Microalgae biomass incorporation in pasta products," 5th Pigments in Food congress—for quality and health, ISBN 978-952-10-4846-3, p. 182, (Aug. 2008). Abstract.
Gouveia et al., "Chlorella vulgaris and Haematococcus pluvialis biomass as colouring and antioxidant in food emulsions," Eur Food Res Technol, 222:362-367, (2006).
Gouveia, L. et al., "Microalgae in Novel Food Products," Food Chemistry Research Developments, Chapter 2, Nova Science Publishers, Inc., ISBN 978-1-60456-262-0, 37 pages, (May 2008).
Krüger, "Kurze Charakteristik einiger niedrerer Organismen im Saftfluss der Laubbäume," Hedwigia, 33: 241-266, (1894). Machine Translation.
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of Chlorella Protothecoides," J. Biotech., 110:85-93, (2004).
Raymundo et al., "Fat mimetic capacity of Chlorella vulgaris biomass in oil-in-water food emulsions stabilized by pea protein," Food Research International, 38:961-965, (Feb. 25, 2005).
Ryckebosch, Eline et al., "Influence of Drying and Storage on Lipid and Carotenoid Stability of Microalga *Phaeodactylum tricornutum*", Journal of Agricultural and Food Chem., 2011, 59:11063-11069 accessed at https://pubs.acs.org/doi/pdf/10.1021/jf2025456 (Year: 2011).
Shi et al., "Production and rapid extraction of lutein and the other lipid-soluble pigments from Chlorella protothecoides grown under heterotrophic and mixotrophic conditions," Nahrung, 43:109-113, (1999).
Shi, et al., "Production of biomass and lutein by Chlorella protothecoides at various glucose concentrations in heterotrophic cultures", Process Biochemistry, 34:341-347, (1999).
Solazyme, Inc. "Algal Flour (*Chlorella*) GRAS Notice," Mar. 16, 2010, pp. 1-74, retrieved from the internet on May 23, 2014t: http://www.fda.gov/ucm/groups/fdagov-public/@fdagov-foods-gen/documents/document/ucm269513.pdf.
Watson, Elaine, et al., "Solazyme Breaking News on Food & Beverage Development—North America Special Edition: Protein-Rich Foods . . . The Next Generation Could Algae be the Next Big Thing in Protein Market? Part one: Solazyme Roquette Nutritionals." URL:http://www.foodnavigator-usa.com/contenUview/prinU733996, Jan. 23, 2013.
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (Mar. 1, 1994).
Xu, H., et al., "High Quality Biodiesel Production from a Microalgal Chlorella Protothecoides by Heterotrophic Growth in Fermenters." Journal of Biotechnology, vol. 126, pp. 499-507, (2006).
Bisten A and H.Schuchmann, "Optical measuring methods for the investigation of high-pressure homogenization", Processes, (Nov. 15, 2016) ;4(4):41.
Memorandum Order, *Roquette Frères, S.A.* v. *Solazyme, Inc.*, C.A. No. 14-1442-SLR, District Court for the District of Delaware, Jan. 12, 2016.
Plaintiff and Counter-Defendant Roquette Frères, S.A.'s Reply Brief in Support of Its Motion for Stay Pending Appeal, *Roquette Frères, S.A.* v. *Solazyme, Inc.*, C.A. No. 14-1442-SLR, District Court for the District of Delaware, Jan. 8, 2016.
Defendant and Counterclaimant Solazyme, Inc.'s Brief in Opposition to Plaintiff and Counter-Defendant Roquette Freres, S.A.'s Motion to Stay Pending Appeal, *Roquette Frères, S.A.* v. *Solazyme, Inc.*, C.A. No. 14-1442-SLR, District Court for the District of Delaware, Jan. 6, 2016.
Declaration of Jonathan Wolfson in Support of Defendant and Counterclaimant Solazyme, Inc.'s Opposition to Plaintiff and Counterclaimant Roquette Freres, S.A.'s Motion to Stay Pending

(56) References Cited

OTHER PUBLICATIONS

Appeal, *Roquette Frères, S.A. v. Solazyme, Inc.*, C.A. No. 14-1442-SLR, District Court for the District of Delaware, Jan. 6, 2016, Redacted Public Version.
Declaration of Jeffrey M. Goehring in Support of Plaintiff and Counter-Defendant Roquette Frères, S.A.'s Brief Motion for Stay Pending Appeal, *Roquette Frères, S.A. v. Solazyme, Inc.*, C.A. No. 14-1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted in its Entirety.
Motion to Stay Pending Appeal and Order Granting Motion to Stay Pending Appeal, *Roquette Frères, S.A. v. Solazyme, Inc.*, C.A. No. 14-1442-SLR, District Court for the District of Delaware, Dec. 28, 2015.
Memorandum of Law in Support of Motion by Roquette Frères, S.A. for a Stay Pending Appeal, *Roquette Frères, S.A. v. Solazyme, Inc.*, C.A. No. 14-1442-SLR, District Court for the District of Delaware, Dec. 28, 2015.
Email dated Nov. 3, 2015, from Gerald Suh of Solazyme, Inc., to Jeffrey M. Goehring of Young & Thompson International Patent & Trademark Law (counsel for Roquette Frères, S.A.).
Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: • Exhibits 1, 9-12, and 14-15 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 141, Jun. 22, 2015, Redacted Version • Exhibits 2-8 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-1, Jun. 22, 2015 • Exhibit 13 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-2, Jun. 22, 2015 • Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112, Jun. 22, 2015 • Roquette Frères, S.A.'s Opening Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 140, Jun. 22, 2015, Redacted Version.
Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.
Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).
Opinion dated Dec. 21, 2015 in *Roquette Frères, S.A., v. Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.
Youzhi Jiagong, (Jun. 8, 2007), "Oil Processing Technology (2nd edition)", Chemical Industry Press, Title page., Publication Page, Table of Contents, pp. 206-213, (in Chinese).
"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Auxenochlorella", article from Wikipedia, Retrieved from the Internet on Mar. 23, 2016, "https://en.wikipedia.org/w/index.php?title=Auxenochlorella&oldid=711518993".
Clore, G.M. and E.M. Chance, A computer analysis of cyanide stimulated oxygen uptake in *Chlorella Protothecoides*. (Jul. 1977) FEBS Lett. 79 (2):353-356.
"Algen—Nudein ais Altmark Spezialitat (Algae noodles: a speciality from Altmark region)" in German language, and other *Chlorella* Food products, (Oct. 9, 2007), 3 pages.
Imai, Ichiro, et al. "Advanced research on Shellfish poisonings: Current Status and overview", Table of Contents, Chapters 1 and Chapter 4, 11 pages.
"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].
Lee, Yuan-Kun, "Commercial Production of microalgae in the Asia-Pacific rim", Journal of Applied Phycology, 9:403-411, (Oct. 29, 1997).
Kay, Robert A., "Microalgae as Food and Supplement", Critical Reviews in Food Science and Nutrition, 30(6):555-573 (Feb. 1991).
Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).
"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.
Hirashima, Ryuta, "Framework of evaluation on inventive step requirement and significance of 'technical problem'", Patent 2010, 63(5): 34-49 (in Japanese; no translation).
Ullmann, Jorg, "The Difference between *Chlorella* vulgaris and *Chlorella* pyrenoidosa", (2006) (http://www.algomed.de/index.php?op=algenfarm_geschichte).
"History of the algae farm: Chlorella Algae—Roquette Klötze GmbH", [Retrieved from the Internet Nov. 25, 2016: <URL: (http://www.algomed.de/index.php?op=algenfarm_geschichte)].
Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.
Oral Summary, dated Nov. 7, 2016, for Invalidation Hearing for Japanese Patent No. 5731982 (in Japanese).
Oral Summary by the Patentee, dated Nov. 29, 2016, for Invalidation Hearing for Japanese Patent No. 5731982 (in Japanese).
USDA National Nutrient Database (https://ndb.nal.usda.gov/ndb/).
Environmental Stresses in Non Mammalian Organisms, p. 29. with English translation.

(56) References Cited

OTHER PUBLICATIONS

Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).
Solazyme Market and Products, (2005).
Letter from Susan Cho to Susan Carlson, dated Jul. 25, 2011 and "RF1's Chlorella vulgaris GRAS Self affirmation (dated Jul. 16, 2010)."
[Retrieved from the Internet Oct. 13, 2016: <URL: http://hfnet.nih.go.jp/contents/detail105.htm] (in Chinese).
"Roquette Freres, S.A. and Solazyme, Inc. Agree to Dissolve Microalgae Join Venture", (Jun. 24, 2013) Press Release, Lestrem, France.
Standard Tables of Food Composition in Japan 2015 (Seventh Revised Edition), Table of Fatty Acid Composition, Edited by the Council for Science and Technology, the Ministry of Education, Culture, Sports, Science and Technology, (available from http://www.mext.go.jp/a_menu/syokuhinseibun/1365295.htm) [Retrieved from the Internet Oct. 12, 2016: <URL: (http://www.algomed.de/index.php?op=algenfarm_geschichte)] http://www.geocities.jp/jr2bvb/syokuhin/sibousan/oil_s.htm].
"'Taste' of Lipids?" [Retrieved from the Internet Oct. 12, 2016: <URL: (https://sites.google.com/site/coffeetambe/coffeescience/physiology/taste/fat] with English Machine Translation.
Japanese Laid-Open Publication No. 2000-175680 (translator's note: an English language member of the same patent family: EP 1142985 (A1)).
Japanese Laid-Open Publication No. 2002-223787 (translator's note: no English language counterpart could be located).
http://mcc.nies.go.jp/strainList.do?strainId=2555&condition=Auxenochlorella+protothecoides.
http://mcc.nies.go.jp/strainList.do?strainId=2568&condition=Auxenochlorella+protothecoides.
*Roquette Freres S.A. v. Solazyme Inc.*, Delaware District Court, Case No. 1:14-cv-01442 District Judge Sue L. Robinson, presiding, Solazyme, Inc.'s Answer to Plaintiff Roquette Freres, S.A.'s Complaint, Petition to Confirm Arbitration Award and Counterclaims, filed Feb. 26, 2015, 29 pages.
Joint Venture and Operating agreement of Solazyme Roquette Nutritionals, LLC., copy dated Nov. 7, 2015.
*Solazyme, Inc.* vs. *Roquette Freres, S.A.*, Arbitration Award, dated Feb. 19, 2015.
Request for Invalidation, dated Jan. 7, 2015, for Chinese Patent Application No. 200980149978.1, 21 pages (in Chinese).
Supplemental Statement for Request for Invalidation, dated Dec. 2, 2015, for Chinese Patent Application No. 200980149978.1, 35 pages (in Chinese), including the list of submitted Counter Evidences on p. 1-2.
Notification of Acceptance of Request for Invalidation, dated Jan. 28, 2016, for Chinese Patent Application No. 200980149978.1, 4 pages (in Chinese).
Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater discharge from a chemical pertilizer plant by Chlorella protothecoides USTB-01", Chinese Journal of Environmental Engineering, (Apr. 2010), 4(4):737-740 (in Chinese).
Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", pp. 155 (and Chinese translation thereof) • Singelton Paul and Diana Sainsbury, "Dictionary of Microbiological and Molecular Biology, (2nd Ed. 1987)", pp. 178-179 (and Chinese translation thereof).
Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).
Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).
• Exhibit MB-1, Federal Court of Australia, Practice Note CM7, Expert Witnesses in Proceedings on the Federal Court of Australia, commenes Jun. 4, 2013 • Exhibit MB-2, Michael Armin Borowitzka Curriculum Vitae • Exhibit MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • Exhibit MB-4, Krauss, Robert W., "Mass Culture of Algae for Food and Other Organic Compounds," American Journal of Botany, vol. 49, No. 4 (Apr. 1962), pp. 425-435. • Exhibit MB-5, Lee, Yuan-Kun, "Commercial Production of microalgae in the Asia-Pacific rim", Journal of Applied Phycology, 9:403-411, (Oct. 29, 1997) • Exhibit MB-6, Soong, Pinnan, "Productions and Development of *Chlorella* and *Spirulina* in Taiwan", Algae Biomass: Production and Use, Gedaliah Shelef and Carl J. Soeder (eds.), North-Holland Biomedical Press, (Dec. 1980), pp. 97-113 and title and copyright page. • Exhibit MB-7, Kawaguchi, Kotaro, "Microalgae Production Systems in Asia", Algae Biomass: Production and Use, Gedaliah Shelef and Carl J. Soeder (eds.), North-Holland Biomedical Press, (Dec. 1980), pp. 25-33 and title and copyright page. • Exhibit MB-8, Kay, Robert A., "Microalgae as Food and Supplement", Critical Reviews in Food Science and Nutrition, 30(6):555-573 (Feb. 1991). • Exhibit MB-9, Raymundo et al., "Fat mimetic capacity of Chlorella vulgaris biomass in oil-in-water food emulsions stabilized by pea protein," Food Research International, 38:961-965, (Feb. 25, 2005). • Exhibit MB-10, Samejima, H. and J Myers, "On the Heterotrophic Growth of Chlorella *pyrenoidosa*", J. Gen Microbiol, (1958), 18:107-117.
• Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. • Exhibit MB-12, Becker, E.W., "Micro-algae as a source of protein," Biotechnology Advances, 25:207-201, (Mar.-Apr. 2007). • Exhibit MB-13, Iwamoto, Hiroaki, "Industrial Production of Microalgal Cell-mass and Secondary Products—Major Industrial Species *Chlorella*", Chapter 11, Handbook of Microalgal Culture: Biotechnology and Applied Phycology, Amos Richmond (eds), (Dec. 1, 2003), pp. 255-263. • Exhibit MB-14, Petkov et al., "Which are fatty acids of the green alga Chlorella?," Biochemical Systematics and Ecology, 35:281-285, (2007). • Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777. • Exhibit MB-16, Xu et al., "High Quality Biodiesel Production From a Microalga Chlorella Protothecoides by Heterotrophic Growth in Fermenters," Journal of Biotechnology, 126(4):499-507, (May 2006). • Exhibit MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). • Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
• Exhibit MB-19, Australian Application No. 2009303354B2 from International Patent Application No. PCT/US2009/060692, naming Solazyme, Inc., International Patent Publication No. 2010/045368, dated Apr. 22, 2010. • Exhibit MB-20, Pabst, W., "Nutritional evaluation of nonsewage microalgae by the rat balance method," Arch. HyrobioL Beih, (Dec. 1978), pp. 65-70 • Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).
• Exhibit MB-22, Kamiya, "Effects of Blue Light and Ammonia on Nitrogen Metabolism in a Colorless Mutant of Chlorella", Plant Cell

(56) References Cited

OTHER PUBLICATIONS

Phyiol., 30(4):513-521 (1989) • Exhibit MB-23, Biello et al., "Biofuel of the Future: Oil from Algae," Scientific American, 2 pages, (Jan. 9, 2008).
Evidence in Support, in the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh in the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages) • Exhibit YS1, Arbitration Award, *Solazyme Inc.* vs. *Roquette Frères*, Case 1:14-cv-01442-SLR, Document 153, Filed Dec. 21, 2015 • Exhibit YS2, French Patent Publication No. FR 2 924 126, filed Nov. 28, 2007. • Exhibit YS3, Memorandum Opinion, Document 153, *Roquette Frères, S.A.* vs. *Solazyme Inc.*, Case 1:14-cv-01442-SLR, filed Dec. 21, 2015.
Declaration of Craig Patch in the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) • Exhibit CP-1, Federal Court of Australia, Practice Note CM7, Expert Witnesses in Proceedings on the Federal Court of Australia, commences Jun. 4, 2013. • Exhibit CP-2, Craig Patch Curriculum Vitae.
Declaration of Craig Patch in the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). • Exhibit CP3, Record of Views Formed in Response to Inquires, updated Mar. 2015 (20 pages) • Exhibit CP4, Huss, V.A.R., et al., "Biochemical Taxonomy and Molecular Phylogeny of the Genus Chlorella Sensu Lato (Chlorophyta)1", J. Phycol. 35, 587-598 (Jan. 15, 1999).
Evidence in Answer, in the matter of Australian Patent Application No. 2009303354 in the name of Solazyme, Inc. and Opposition by *Roquette Frères, S.A.* v. *Solazyme, Inc.*, Commonwealth of Australia, Sep. 29, 2016, (1 page).
Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia, Dec. 21, 2016, (14 pages).
Evidence in Reply, In the matter of Australian Patent Application No. 2009303354 in the name of Solazyme, Inc. and Opposition by *Roquette Frères, S.A.* v. *Solazyme, Inc.*, Commonwealth of Australia Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.
Freshwater Algae Culture Collection at the Institute of Hydrobiology (FACHB-collection), certification letter by the Chinse Academy of Science, "Chlorella vulgaris", (No Date).
Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response to Reg 5.23 Request, in the Matter of Australian Patent Application No. 2009303354 in the name of Corbion Biotech, Inc., filed Feb. 5, 2018, 18 pages. • Letter from David Sieveking, dated Jan. 24, 2018 Statutory Declaration of Dr. Daniel Peter Sieveking, dated Jan. 24, 2018. • Exhibit DS-1, Kyle, David, "Production and Use of Lipids from Microalgae", Microalgal Lipids, Lipid Technology, (May-Jun. 1992), pp. 59-64. • Exhibit DK-2, Chen et al., "High cell density culture of microalgae in heterotrophic growth," Trends in Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLA0043JP-0807X01JP].
Request for Withdrawal of Opposition, by Roquette Freres, to Grant of Australian Patent Application No. 2009303354, in the Name of Corbion Biotech, Inc., dated Mar. 13, 2018.
Opposition Proceedings, dated Mar. 14, 2018, Acknowledgement of the the Request for Withdrawal of Opposition, by Roquette Freres, to Grant of Australian Patent Application No. 2009303354.
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).

* cited by examiner

GRANULES OF PROTEIN-RICH MICROALGAL BIOMASS FLOUR AND METHOD FOR PREPARING SAME

The present invention relates to granules of protein-rich microalgal biomass flour, said biomass being of intact (unmilled) microalgae.

More particularly, the present invention relates to granules of microalgal biomass flour having a particle size distribution and compressibility and aerated density properties that are entirely noteworthy.

The present invention relates to granules of microalgal biomass flour having entirely satisfactory flow and wettability properties.

The present invention also relates to the process for preparing these granules of protein-rich microalgal biomass flour.

Finally, the present invention relates to the use of the granules of microalgal biomass flour in food for human consumption and animal feed (pets, aquaculture, etc.), or for applications in the pharmaceutical and cosmetics industry.

There are several species of algae that can be used in food, most being "macroalgae" such as kelp, sea lettuce (*Ulva lactuca*) and red algae for food, of the type *Porphyra* (cultivated in Japan) or "dulse" (red alga *Palmaria palmata*).

However, besides these microalgae, there are also many sources of algae represented by the "microalgae", in particular photosynthetic or nonphotosynthetic single-cell microscopic algae of marine or nonmarine origin, cultivated for their applications in biofuel or food.

For example, spirulina (*Arthrospira platensis*) is cultivated in open lagoons (by phototrophy) for use as a food supplement or incorporated in small amounts into confectionery or drinks (generally less than 0.5% w/w).

Other microalgae, including certain species of *Chlorella*, are also very popular in Asian countries as food supplements.

The present invention thus relates to the microalgal biomass suitable (or appropriate) for human consumption which is rich in nutrients, in particular in proteins.

The invention relates to a protein-rich microalgal biomass flour which can be incorporated into food products in which the protein content of the microalgal flour can totally or partially replace the proteins present in conventional food products.

The microalgal biomass flour also provides other benefits, for instance micronutrients, dietary fibers (soluble and insoluble carbohydrates), triglycerides, phospholipids, glycoproteins, phytosterols, tocopherols, tocotrienols, and selenium.

For the purposes of the invention, the microalgae under consideration are the species which produce proteins at highly rich levels.

The microalgal biomass comprises at least 50% by dry weight of proteins, preferably between 50% and 70% by dry weight of proteins.

The preferred microalgae of the invention can, for their part, grow under heterotrophic conditions (on sugars as carbon source and in the absence of light).

The applicant company recommends selecting protein-rich microalgae of the *Chlorella* genus.

*Chlorella* is a single-cell green microalga, belonging to the chlorophyte branch.

Preferably, the microalgae used according to the invention are of *Chlorella sorokiniana* or *Chlorella protothecoides* type.

The microalgae are cultivated in a liquid medium for producing the biomass as such.

According to the invention, the microalgae are cultivated in a medium containing a carbon source and a nitrogen source in the absence of light (heterotrophic conditions).

The solid and liquid growth media are generally available in the literature, and the recommendations for preparing the particular media which are suitable for a large variety of microorganism strains can be easily found, for example, online at http://www.utex.org/, a site maintained by the University of Texas at Austin for its culture collection of algae (UTEX).

The production of biomass is carried out in fermenters (or bioreactors).

The specific examples of bioreactors, the culture conditions, and the heterotropic growth and the propagation methods can be combined in any appropriate manner in order to improve the efficiency of the microbial growth and the production of proteins.

In order to prepare the biomass for use in food, the biomass obtained at the end of fermentation is concentrated or harvested from the fermentation medium.

At the time that the microalgal biomass is harvested from the fermentation medium, the biomass comprises intact cells mostly in suspension in an aqueous culture medium.

In order to concentrate the biomass, a step of solid-liquid separation by filtration or by centrifugation, taken alone or in combination, is then carried out by any means known, moreover, to those skilled in the art.

After concentration, the microalgal biomass can be processed in order to produce vacuum-packed cakes, algal flakes, algal homogenates, algal powder or algal flour.

In accordance with the invention, the microalgal biomass is dried in order to facilitate the subsequent processing or for use of the biomass in its various applications.

Various textures and flavors can be conferred on food products, depending on whether the algal biomass is dried, and if it is, according to the drying method used.

For example, patent U.S. Pat. No. 6,607,900 describes the drying of the microalgal biomass using a drum-drier without prior centrifugation, in order to prepare microalgal flakes.

Microalgal powder can be prepared from the microalgal biomass concentrated using a pneumatic drier or by spray-drying, as described in patent U.S. Pat. No. 6,372,460.

In a spray-drier, a liquid suspension is then sprayed in the form of a dispersion of fine droplets in a heated air stream. The material entrained is rapidly dried and forms a dry powder.

In certain cases, a pulse combustion drier can also be used in order to obtain a powdery texture in the dried final material.

In yet other cases, a combination of spray-drying followed by the use of a fluidized bed drier is implemented in order to achieve optimum conditions for obtaining a dried microbial biomass (see, for example, patent U.S. Pat. No. 6,255,505).

In the technical field addressed by the invention, the intention is to prepare an algal biomass flour from the microalgal biomass that has been concentrated and then spray-dried or flash-dried.

After drying, the water content or moisture content of the powder is generally less than 10% by weight.

However, in the conventional processes for recovering protein-rich microalgal biomass, the obtaining of a dry powder of low compressibility and low bulk density is highly undesirable.

There is therefore still an unsatisfied need for novel forms of protein-rich microalgal biomass flour in order to make it possible to easily incorporate them, on a large scale, into food products which must remain delicious and nutritious.

The applicant company has therefore found that this need can be satisfied by providing granules of microalgal biomass flour having a particle size distribution and compressibility and bulk density properties that are entirely noteworthy.

The granules of microalgal biomass flour in accordance with the invention are thus characterized in that they have:
- a particle size distribution, measured on an LS laser particle size analyzer of the COULTER® brand, having a Dmode of between 60 and 300 μm and a D4,3 between 70 and 420 μm,
- a bulk density, measured on a HOSOKAWA Powder Characteristics Tester, of between 0.60 to 0.70 g/mL,
- a compressibility, measured on a HOSOKAWA Powder Characteristics Tester, of between 15% and 25%, preferably between 18% and 21%.

The granules of microalgal biomass flour according to the invention are first characterized by their particle size distribution.

This measurement is carried out on an LS laser particle size analyzer of the COULTER® brand, equipped with its small volume dispersion module or SVM (125 ml), according to the constructor's specifications (in the "*Small Volume Module Operating instructions*").

The particle size distributions are illustrated by the Dmode (diameter of the main population) values and the D4,3 (arithmetic mean diameter) values.

The granules of microalgal biomass flour in accordance with the invention then have a monomodal particle size distribution, characterized by a Dmode of between 60 and 300 μm and a D4,3 of between 70 and 420 μm.

More particularly, the granules of microalgal biomass flour according to the invention can be classified into two families, depending on their microalgal origin:
- the first family of granules of *Chlorella sorokiniana* biomass flour has a Dmode of between 70 and 130 μm and a D4,3 between 75 and 140 μm;
- the second family of granules of *Chlorella protothecoides* biomass flour has a Dmode of between 200 and 280 μm and a D4,3 between 300 and 420 μm.

The granules of microalgal biomass flour in accordance with the invention also have a bulk density, measured on a HOSOKAWA Powder Characteristics Tester, of between 0.60 to 0.70 g/mL and a compressibility, measured on a HOSOKAWA Powder Characteristics Tester, of between 15% and 25%, preferably between 18% and 21%.

The tapped density, bulk density and compressibility values of the granules of microalgal biomass flour according to the invention are determined using the Powder Characteristics Tester device type PTE sold by the company HOSOKAWA, according to the constructor's specifications.

This device makes it possible to measure, under standardized and reproducible conditions, the flowability of a powder by measuring in particular the bulk density and the bulk tapped density and then calculating, from these data, the compressibility values by means of the following formula:

$$\text{Compressibility (\%)} = \frac{(\text{tapped density} - \text{bulk density})}{\text{tapped density}} \times 100$$

The tapped density and bulk density measurements are carried out on the Powder Characteristics Tester device type PTE, as mentioned above, according to the method recommended in the operating instructions for said POWDER TESTER (setting by default on 180 shakes for measuring the tapped density).

This bulk density value is all the more noteworthy since the granules of microalgal biomass flour in accordance with the invention have a higher bulk density than the flour of microalgae dried conventionally.

Indeed, it is accepted that the density of a product will be all the lower if it is granulated by spray-drying.

However, although granulated, the products in accordance with the invention have a higher bulk density than expected: by way of comparison, as will be exemplified hereinafter, the bulk densities of microalgal flour powders spray-dried conventionally have a lower bulk density, of between 0.35 and 0.50 g/ml.

The granules of microalgal biomass flour according to the invention also have entirely satisfactory flow properties, according to a test A.

The test A consists in measuring the degree of cohesion of the granules of microalgal flour according to the invention.

This cohesion test takes its inspiration from the cohesion test also described in the "Operating Instructions" of the Powder Characteristics Tester type PTE sold by the company HOSOKAWA.

The test A consists first of all in sieving the granules of microalgal biomass flour according to the invention on a sieve with a mesh size of 800 μm.

The granules which have a size of less than 800 μm are then recovered and introduced into a closed container, and undergo mixing by epicycloidal movement using a laboratory mixer of the TURBULA brand, type T2C.

By virtue of this mixing, the granules of microalgal biomass flour in accordance with the invention will, according to their own characteristics, express their propensities to agglomerate or to repel one another.

The granules thus mixed are then deposited on a column of three sieves (2000 μm; 1400 μm; 800 μm) for further sieving.

Once the sieving has ended, the oversize on each sieve is quantified and the result gives an illustration of the "cohesive" or "tacky" nature of the granules of microalgal biomass flour.

Thus, a free-flow, and therefore weakly cohesive, powder of granules will be virtually unstopped by the sieves of large mesh size, but will be increasingly stopped as the meshes of said sieves become tighter.

The protocol is the following:
- sieve the necessary amount of product on an 800 μm sieve so as to recover 50 g of product of size less than 800 μm,
- introduce these 50 g of granules of size less than 800 μm into a glass jar with a capacity of one liter (ref. BVBL Verrerie Villeurbannaise-Villeurbanne France) and close the lid,
- place this jar in the TURBULA model T2C mixer set to the speed of 42 rpm (Willy A. Bachofen Sarl-Sausheim-France) and mix for 5 minutes,
- prepare a column of three sieves (of the Saulas brand —diameter 200 mm; Paisy Cosdon—France) which will be placed on a Fritsch sieve shaker, model Pulverisette type 00.502; details of the assembly starting from the bottom to the top: sieve shaker, sieve base, 800 μm sieve, 1400 μm sieve, 2000 μm sieve, sieve shaker lid,
- deposit the powder resulting from the mixing on the top of the column (2000 μm sieve), close with the sieve shaker lid and sieve for 5 minutes on the FRITSCH sieve shaker, with an amplitude of 5 in the continuous position, weigh the oversize on each sieve.

The granules of microalgal biomass flour according to the invention then exhibit no oversize on each of these sieves, reflecting a free flow entirely in accordance with what is obtained for the powders of protein-rich microalgae of the prior art.

Finally, the granules of microalgal biomass flour according to the invention are characterized by a satisfactory degree of wettability, measured according to a test B.

Wettability is a technological property that is very often used to characterize a powder resuspended in water, for example in the dairy industries.

It conveys the ability of a powder to become immersed after having been deposited at the surface of water (Haugaard Sorensen et al., 1978, "Méthodes d'analyse des produits laitiers déshydratés" ["Methods for analyzing dehydrated dairy products"], Niro A/S (ed.), Copenhagen, Denmark), and thus reflects the capacity of the powder to absorb water at its surface (Cayot and Lorient, 1998, "Structures et technofonctions des protéines du fait" ["Structures and technofunctions of milk products"]. Paris: Airlait Recherches: Tec and Doc, Lavoisier).

The determination of this index consists in measuring the time necessary for a certain amount of powder to penetrate into the water through its free surface at rest.

It is also necessary to associate with the wettability the ability of the powder to swell. Indeed, when a powder absorbs water, it gradually swells. Then, the structure of the powder disappears when the various constituents are solubilized or dispersed.

Among the factors that influence wettability are the presence of large primary particles, the reintroduction of the fines, the density of the powder, the porosity and the capillarity of the powder particles and also the presence of air, the presence of fats at the surface of the powder particles and the reconstitution conditions.

The test B, developed by the applicant company, consists in this case in considering more particularly the behavior of the microalgal flour powder when brought into contact with water, by measuring, after a certain contact time, the height of the powder which decants when placed at the surface of the water.

The protocol for this test is the following:

introduce 500 ml of demineralized water at 20° C. into a 600 ml squat-form beaker (FISCHERBRAND FB 33114 beaker), place 25 g of the microalgal flour powder uniformly at the surface of the water, without mixing, observe the behavior of the powder after 3 h of contact, measure the height of the product decanted at the bottom of the beaker.

A very cohesive, tacky, low-wettability powder will remain at the surface of the liquid, whereas a powder of better wettability, which is less tacky, will decant more readily.

The granules of microalgal biomass flour according to the invention then have a degree of wettability, expressed according to this test B, by the height of the product decanted in a beaker, at a value of between 5 and 25 mm.

More particularly:
the first family has a decanted product height of between 5 and 15 mm,
the second family has a decanted product height of between 15 and 25 mm.

The granules of microalgal biomass flour according to the invention are also characterized by their specific surface area.

The specific surface area is determined over the whole of the particle size distribution of the granules of microalgal biomass flour by means of a Quantachrome specific surface area analyzer based on a test for absorption of nitrogen onto the surface of the product subjected to the analysis, carried out on an SA3100 device from Beckmann Coulter, according to the technique described in the article BET Surface Area by Nitrogen Absorption by S. BRUNAUER et al. (Journal of American Chemical Society, 60, 309, 1938).

The granules of microalgal biomass flour in accordance with the invention, after degassing for 30 minutes at 30° C. under vacuum, then have a specific surface area of between 0.45 and 0.70 $m^2/g$.

More particularly, the first family of granules of microalgal biomass flour has a specific surface area, according to the BET method, of between 0.45 and 0.50 $m^2/g$.

As regards the second family of granules of microalgal biomass flour, it has a specific surface area, according to the BET method, of between 0.60 and 0.70 $m^2/g$.

The granules of microalgal biomass flour of the invention differ from the microalgal flours obtained by conventional spray-drying.

The granules of microalgal biomass flour in accordance with the invention are capable of being obtained by means of a particular spray-drying process, which uses high-pressure spray nozzles in a parallel-flow tower which directs the semi-dry particles toward the bottom, toward a moving belt.

The material is then transported as a porous layer through post-drying and cooling zones, which give it a crunchy structure, like that of a cake, which breaks at the end of the belt and is discharged, usually via a particle size final control system.

In order to carry out the granulation of the algal biomass flour, by following this spray-drying principle, a FILTERMAT™ spray-drier sold by the company GEA NIRO or a TETRA MAGNA PROLAC DRYER™ drying system sold by the company TETRA PAK can, for example, be used.

Surprisingly and unexpectedly, the applicant company has thus noted that the granulation of the microalgal biomass flour by implementing, for example, this FILTERMAT™ process, makes it possible to prepare, with a high yield, a product in accordance with the invention in terms of particle size distribution, of its bulk density and of its compressibility.

Indeed, the processes previously described (such as single-effect spray-drying or multi-effect spray-drying—MSD tower) do not make it possible to obtain all of the desired characteristics.

The process for preparing the granules of microalgal biomass flour in accordance with the invention therefore comprises the following steps:

1) preparing a suspension of protein-rich microalgal biomass in water at a solids content of between 10% and 35% by dry weight,
2) spraying it in a vertical spray-drier equipped with a moving belt at its base, and with a high-pressure nozzle in its upper part, while regulating:
    the first temperature of the primary air at a value of between 160 and 220° C.,
    the second temperature of the primary air at a value of between 90 and 150° C.,
    the spray pressure at a value of between 50 and 250 bar, preferably between 80 and 150 bar, 3) regulating the entry temperature of the post-drying zone on the moving belt at a value of between 70 and 90° C., and regulating the temperature of the cooling zone at a value of between 15 and 25° C., 4) collecting the granules of microalgal biomass flour thus obtained.

The first step of the process of the invention consists in preparing a protein-rich microalgal biomass suspension in water at a solids content of between 10% and 35% by dry weight.

The microalgae chosen in order to illustrate the process in accordance with the invention are:

*Chlorella sorokiniana* (UTEX 1663 strain—The Culture Collection of Algae at the University of Texas at Austin—USA),

*Chlorella protothecoides* (UTEX 250 strain—The Culture Collection of Algae at the University of Texas at Austin—USA).

As will be exemplified hereinafter, the biomasses extracted from the fermentation medium by any means known to those skilled in the art (for example by centrifugation) are then deactivated by flash heat treatment.

The second step of the process of the invention consists in spraying the suspension of biomass in a vertical spray-drier equipped with a moving belt at its base, and with a high-pressure nozzle in its upper part, while at the same time regulating:

the first temperature of the primary air at a value of between 160 and 220° C., the second temperature of the primary air at a value of between 90 and 150° C., the spray pressure at a value of between 50 and 250 bar, preferably between 80 and 150 bar.

The third step of the process of the invention consists in regulating the entry temperature of the post-drying zone on the moving belt to a value of between 70 and 90° C., and regulating the temperature of the cooling zone to a value of between 15 and 25° C.

The granules of microalgal biomass flour have, on exiting the main chamber, a residual moisture content of between 8% and 15%.

In order to bring the degree of moisture of the microalgal flour granules to the desired value (on exiting the drier: between 3% and 6%), the applicant company has found that it is necessary to adhere to these temperature scales of the drying and cooling zones.

The final step of the process in accordance with the invention consists, finally, in collecting the granules of microalgal biomass flour thus obtained.

The microalgal flour granules in accordance with the invention can be used, owing to the quality of their functional properties mentioned above, in applications in food for human consumption and animal feed (pets, aquaculture, etc.), or in applications of the pharmaceutical and cosmetics industry. It is important to note that, with the term "pharmaceutical industry", the microalgal flour granules in accordance with the invention are not used as an active ingredient, but as formulating agents, for preparing tablets.

Thus, the present invention also relates to a method for preparing human food compositions or animal feed compositions or pharmaceutical or cosmetic compositions, comprising a step of incorporating microalgal flour granules in accordance with the invention.

The microalgal flour granules in accordance with the invention are thus of great interest from the viewpoint of their functional properties:

their free flow (already agglomerated, less fine powder) makes it possible to facilitate feeding of an extruder and the filling of hoppers;

their higher bulk density makes it possible to also facilitate their transportation (reduced cost), and to reduce the emission of dust during handling of the powder bags;

their easy dispersion in liquids makes it possible:
  to avoid the formulation of lumps,
  to facilitate the preparation for drinks,
  to incorporate them into viscous media, without the formation of lumps or the need for powerful "dispersers" such as gums;

their ability to be compressed means they are meant for the manufacture of insoluble solid granules, resistant to the process for manufacturing the foods which make it possible, for the green microalgal flour granules according to the invention, to create attractive green flecked products (cake, cookie, tablets, gums, coating, etc.).

For example, in the food supplement field, the granules of microalgal biomass flour can be easily incorporated into orodispersible tablets, which are galenical forms suitable for example for pediatrics and geriatrics.

By way of illustration, the applicant company has combined the microalgal flour granules according to the invention with one of its rapid disintegration excipients for the formulation of orodispersible tablets: PEARLITOL® Flash.

As will be exemplified hereinafter, the evaluation of the characteristics of these tablets shows that:

there is no negative influence of the incorporation of the granules of microalgal biomass flour on the hardness of the tablets;

the granules of microalgal biomass flour decrease the friability of the tablets.

Other characteristics and advantages of the invention will emerge on reading the examples which follow.

However, they are given here only by way of nonlimiting illustration.

EXAMPLES

Example 1

Production of *C. sorokiniana* in Fed-batch Fermentation with Limiting Glucose Supply The strain used is a *Chlorella sorokiniana* (UTEX 1663 strain—The Culture Collection of Algae at the University of Texas at Austin—USA).

Preculture:
  600 ml of medium in a 2 l Erlenmeyer flask;
  Composition of the medium (table 1 below)

TABLE 1

| | | |
|---|---|---|
| Macro elements (g/l) | Glucose | 20 |
| | $K_2HPO_4 \cdot 3H_2O$ | 0.7 |
| | $MgSO_4\ 7H_2O$ | 0.34 |
| | Citric acid | 1.0 |
| | Urea | 1.08 |
| | $Na_2SO_4$ | 0.2 |
| | $Na_2CO_3$ | 0.1 |
| | Yeast extract | 1 |
| | clerol FBA 3107 (antifoam) | 0.5 |
| Micro elements (mg/l) | $Na_2EDTA$ | 10 |
| | $CaCl_2 \cdot 2H_2O$ | 80 |
| | $FeSO_4 \cdot 7H_2O$ | 40 |

TABLE 1-continued

| | | |
|---|---|---|
| | $MnSO_4 \cdot 4H_2O$ | 0.41 |
| | $CoSO_4 \cdot 7H_2O$ | 0.24 |
| | $CuSO_4 \cdot 5H_2O$ | 0.24 |
| | $ZnSO_4 \cdot 7H_2O$ | 0.5 |
| | $H_3BO_3$ | 0.11 |
| | $(NH4)_6Mo_7O_{27} \cdot 4H_2O$ | 0.04 |

The pH is adjusted to 7 before sterilization by adding 8N NaOH.

The incubation is carried out under the following conditions:
time: 72 h;
temperature: 28° C.;
shaking: 110 rpm (Infors Multitron incubator).

The preculture is then transferred into a Sartorius 30 l fermenter.

Culture for Biomass Production:

The starting medium is similar to that of the preculture:

TABLE 2

| | | |
|---|---|---|
| Macro elements (g/l) | Glucose | 10 |
| | $K_2HPO_4$ | 8 |
| | $MgSO_4\ 7H_2O$ | 0.35 |
| | Citric acid | 1.0 |
| | $(NH_4)_2SO_4$ | 0.2 |
| | $Na_2SO_4$ | 1 |
| | Yeast extract | 3.2 |
| | clerol FBA 3107 (antifoam) | 0.2 |
| Micro elements (mg/l) | $Na_2EDTA$ | 10 |
| | $CaCl_2$ | 100 |
| | $FeSO_4 \cdot 7H_2O$ | 400 |
| | $MnSO_4 \cdot 4H_2O$ | 4.1 |
| | $CoSO_4 \cdot 7H_2O$ | 2.4 |
| | $CuSO_4 \cdot 5H_2O$ | 2.4 |
| | $ZnSO_4 \cdot 7H_2O$ | 5 |
| | $H_3BO_3$ | 1.1 |
| | $(NH4)_6Mo_7O_{27} \cdot 4H_2O$ | 0.4 |

The initial volume (Vi) of the fermenter is adjusted to 13.5 l after inoculation.

It is brought to a final volume of 16-20 l.

The parameters for carrying out the fermentation are the following:

TABLE 3

| | |
|---|---|
| Temperature | 28° C. |
| pH | 6.5 with $NH_3$ 28% w/w |
| $pO_2$ | >20% (maintained by shaking) |
| Shaking | 300 rpm mini |
| Air flow rate | 15 l/min |

When the glucose initially supplied has been consumed, medium is continuously supplied in the form of a concentrated solution containing 500 g/l of glucose and 8 g/l of $MgSO_4.7H_2O$.

The rate of supply is less than the rate of consumption that the strain might carry out, such that the residual content of glucose in the medium is kept at zero, i.e. the growth of the strain is limited by the glucose availability (glucose-limiting condition).

Clerol FBA 3107 antifoam is added on demand in order to prevent excessive foaming.

Results:

After 75 h of culture, 74 g/l of biomass having a protein content (evaluated by N 6.25) of 57% are obtained.

For the rest of the operations, the temperature is maintained below 8-10° C.

After this step, the concentration of the biomass is approximately 18% (dry at cell mass).

Example 2

Drying of the *Chlorella sorokiniana* Biomass

The biomass obtained in example 1 is dried:
in a FILTERMAT device, so as to obtain the microalgal flour granules in accordance with the invention,
in a multi-effect spray-drier (liquid dried in the heat stream and then recovered at the bottom of the tower at the level of the cyclone or of the sleeve filter), so as to obtain a control microalgal flour, in accordance with what is commercially available.

The main operating conditions for multi-effect spray-drying of a suspension of microalgal biomass with a solids content of 18% are the following:
spray pressure (2 nozzles): 150 bar,
entry temperature: 275° C.,
exit temperature: 80° C.,
static bed temperature: 80° C.,
cooling on vibrating fluidized bed:
    1st section entry temperature: 50° C.
    2nd section entry temperature: 20° C.

With regard to the spray-drying process in accordance with the invention, it consists in spraying the biomass at high pressure in a device of FILTERMAT type sold by the company GEA/NIRO, equipped with a high-pressure injection nozzle of DELAVAN type, under the following conditions:
solids content of the microalgal biomass suspension: 18%
first temperature of the primary air: 175° C.+/−10° C.
second temperature of the primary air: 110° C.+/−10° C.
spray pressure: 120 bar
post-drying zone entry temperature: 80° C.
cooling zone temperature: 18° C.
chamber exit temperature: 55° C.+/−2° C.

After drying, the granules of microalgal biomass flour have a residual moisture content of between 3% and 6%.

Example 3

Production of *Chlorella protothecoides* at 28° C. by Fed-batch Fermentation

In order to obtain a high biomass concentration, the glucose is supplied during culture (fed-batch) in order to prevent growth inhibition by glucose.

The salts are supplied at the start of fermentation (batch).

The strain used is *Chlorella protothecoides* UTEX 250 (The Culture Collection of Algae at the University of Texas at Austin—USA).

Preculture:
500 ml of medium in a 2 l Erlenmeyer flask;
Composition of the medium (in g/l):

TABLE 4

| | | |
|---|---|---|
| Macro elements (g/l) | Glucose | 40 |
| | $K_2HPO_4$ | 3 |
| | $Na_2HPO_4$ | 3 |
| | $MgSO_4\ 7H_2O$ | 0.25 |
| | $(NH_4)_2SO_4$ | 1 |
| | Citric acid | 1 |
| | clerol FBA 3107 (antifoam) | 0.1 |

TABLE 4-continued

| | | |
|---|---|---|
| Elements and vitamins | CaCl$_2$•2H$_2$O | 30 |
| | FeSO$_4$•7H$_2$O | 1 |
| | MnSO$_4$•1H$_2$O | 8 |
| | CoSO$_4$•7H$_2$O | 0.1 |
| | CuSO$_4$•5H$_2$O | 0.2 |
| | ZnSO$_4$•7H$_2$O | 0.5 |
| | H$_3$BO$_3$ | 0.1 |
| | Na$_2$MoO$_4$•2H$_2$O | 0.4 |
| | Thiamine HCl | 1 |
| | Biotin | 0.015 |
| | B12 | 0.01 |
| | Calcium pantothenate | 0.03 |
| | p-aminobenzoic acid | 0.06 |

The incubation is carried out under the following conditions: time: 72 h; temperature: 28° C.; shaking: 110 rpm (Infors Multitron incubator).

The preculture is then transferred into a Sartorius 30 l fermenter.

Culture for Biomass Production:

The medium is the following:

TABLE 5

| | | |
|---|---|---|
| Macro elements (g/l) | Glucose | 40 |
| | KH$_2$PO$_4$ | 1.8 |
| | NaH$_2$PO$_4$ | 1.4 |
| | MgSO$_4$ 7H$_2$O | 3.4 |
| | (NH$_4$)$_2$SO$_4$ | 0.2 |
| | clerol FBA 3107 (antifoam) | 0.3 |
| Micro-elements and vitamins (mg/l) | CaCl$_2$•2H$_2$O | 40 |
| | FeSO$_4$•7H$_2$O | 12 |
| | MnSO$_4$•1H$_2$O | 40 |
| | CoSO$_4$•7H$_2$O | 0.1 |
| | CuSO$_4$•5H$_2$O | 0.5 |
| | ZnSO$_4$•7H$_2$O | 50 |
| | H$_3$BO$_3$ | 15 |
| | Na$_2$MoO$_4$•2H$_2$O | 2 |
| | Thiamine HCl | 6 |
| | Biotin | 0.1 |
| | B12 | 0.06 |
| | Calcium pantothenate | 0.2 |
| | p-aminobenzoic acid | 0.2 |

The initial volume (Vi) of the fermenter is adjusted to 17 l after inoculation. It is brought to a final volume of approximately 20 to 25 l.

The parameters for carrying out the fermentation are the following:

TABLE 6

| | |
|---|---|
| Temperature | 28° C. |
| pH | 5.0-5.2 with NH$_3$ 28% w/w |
| pO$_2$ | 20% +/− 5% (maintained by shaking) |
| Shaking | 300 rpm mini |
| Air flow rate | 15 l/min |

When the residual concentration of glucose falls below 10 g/l, glucose is supplied in the form of a concentrated solution at approximately 800 g/l so as to maintain the glucose content between 0 and 20 g/l in the fermenter.

Results 89 g/l of biomass containing 68.5% of proteins are obtained in 40 h.

The cells are deactivated by heat treatment through an HTST zone at 70° C. for 3 minutes.

For the rest of the operations, the temperature is maintained below 8-10° C.

After this step, the concentration of the biomass is approximately 20% (dry cell mass).

Example 4

Drying of the *Chlorella protothecoides* Biomass

The biomass obtained in example 3 is dried:
in a FILTERMAT device, so as to obtain the microalgal flour granules in accordance with the invention,
in a multi-effect spray-drier (liquid dried in the heat stream and then recovered at the bottom of the tower at the level of the cyclone or of the sleeve filter), so as to obtain a control microalgal flour, in accordance with what is commercially available.

The main operating conditions for multi-effect spray-drying of a suspension of microalgal biomass with a solids content of 20% are the following:

spray pressure (2 nozzles): 150 bar,
entry temperature: 270° C.,
exit temperature: 80° C.,
static bed temperature: 80° C.,
cooling on a vibrating fluidized bed:
  1st section entry temperature: 50° C.
  2nd section entry temperature: 20° C.

With regard to the spray-drying process in accordance with the invention, it consists in spraying the biomass at high pressure in a device of FILTERMAT type sold by the company GEA/NIRO, equipped with a high-pressure injection nozzle of DELAVAN type, under the following conditions:

solids content of the microalgal biomass suspension: 20%
first temperature of the primary air: 174° C.+/−10° C.
second temperature of the primary air: 102° C.+/−10° C.
spray pressure: 150 bar
post-drying zone entry temperature: 80° C.
cooling zone temperature: 20° C.
chamber exit temperature: 57° C.+/−3° C.

After drying, the granules of microalgal biomass flour have a residual moisture content of between 3% and 6%.

Example 5

Characterization of the Granules of Microalgal Biomass Flour in Accordance with the Invention Table 7 below presents the physicochemical profile of four batches of microalgal flour granules according to the invention (two batches produced with *Chlorella sorokiniana*—Batches 1 and 2 —and two batches with *Chlorella protothecoides*—Batches 3 and 4), in comparison with flours dried on a multi-effect spray-drier (on an MSD tower).

TABLE 7

|  |  | Chlorella sorokiniana | | | Chlorella protothecoides | | |
| --- | --- | --- | --- | --- | --- | --- | --- |
|  |  | Batch 1 according to the invention | Batch 2 according to the invention | MSD spray-drying control | Batch 3 according to the invention | Batch 4 according to the invention | MSD spray-drying control |
| Solids | % | 92.2 | 91 | 95.2 | 92.8 | 93.2 | 97.3 |
| Protein matter N × 6.25 | % | 54.3 | 54.5 | 48.7 | 62.8 | 62.6 | 60.8 |
| Starch | % | 6.9 | 5.3 | 18.3 | 6.8 | 6.4 | 5.0 |
| Total lipids | % | 9.3 | 8.9 | 8.2 | 10.7 | 12.7 | 14.7 |
| Total chlorophylls | % | 2.49 | 2.15 | 1.97 | <0.05 | <0.05 | Nd |
| Total carotenoids | % | 0.47 | 0.46 | 0.39 | <0.05 | <0.05 | Nd |
| Total sugars | % | 16.6 | 15.4 | 30.1 | 21.3 | 17.9 | 26.1 |

Table 8 below presents in particular the values of the:
*Nd: not detected
  particle size,
  compressibility,
  apparent density,
  specific surface area,
  flow,
  wettability
parameters of the granules of microalgal biomass flour in accordance with the invention, compared with these same parameters in a flour of microalgae dried by conventional spray-drying.

TABLE 8

|  |  | Chlorella sorokiniana | | | Chlorella protothecoides | | |
| --- | --- | --- | --- | --- | --- | --- | --- |
|  |  | Batch 1 according to the invention | Batch 2 according to the invention | MSD spray-drying control | Batch 3 according to the invention | Batch 4 according to the invention | MSD spray-drying control |
| Laser particle size analysis | Dmode μm | 127.6 | 72.9 | 203.5 | 269.2 | 223.4 | 223.4 |
|  | D4,3 μm | 129.4 | 79.3 | 210.1 | 404.8 | 333.6 | 227.8 |
| Specific surface area | $m^2/g$ | 0.45 | 0.48 | 0.5 | 0.62 | 0.65 | Nd |
| bulk density | g/ml | 0.64 | 0.65 | 0.47 | 0.61 | 0.61 | 0.37 |
| tapped density | g/ml | 0.79 | 0.82 | 0.53 | 0.75 | 0.75 | 0.43 |
| compressibility | % | 19 | 20.7 | 11.3 | 18.7 | 18.7 | 14 |
| cohesion 2000 μm | μm | 0 | 0 | 0 | 0 | 0 | 0 |
| cohesion 1400 μm | μm | 0 | 0 | 0 | 0 | 0 | 0 |
| cohesion 800 μm | μm | 0 | 0 | 0 | trace | trace | 0 |
| wettability | mm | 5* | 15** | 20*** | 20* | 20** | 20*** |

For the wettability measurement:

*Chlorella sorokiniana:*

(*) upon introduction of the powder into the beaker, the product migrates slowly to the bottom—at T3h: 5 mm of deposit and about 50% of product at the surface () upon introduction of the powder into the beaker, the product migrates slowly to the bottom—at T3h: 15 mm of deposit and about 20% of product at the surface (*) the product falls directly to the bottom of the beaker at the moment the powder is deposited at the surface of the water.

*Chlorella protothecoides*

(*) the product falls instantaneously to the bottom of the beaker, in a block () at T.3h, all of the product has been deposited in the bottom (*) same observation as for the first test, instead that, at T3h, only a part of the powder has migrated to the bottom and approximately 20% of the product remains at the surface.

Example 6

Incorporation of the Granules of Microalgal Biomass Flour into Orodispersible Tablets In this example, orodispersible tablets are prepared which combine the granules of *Chlorella sorokiniana* biomass flour (batch 1 of example 5) with PEARLITOL® Flash (granulated starch and mannitol) sold by the applicant company.

The production of the tablets is based on the following parameters:

maximum resistance of the beveled flat punches of diameter 13 mm=92 kN.

punch of diameter 13 mm having a surface area (cross section) of 1.327 $cm^2$.

Five different compression forces (expressed as "upper punch force")—of 5, 10, 15, 20 and 25 kN—are applied to the same powder, in order to obtain tablets having five increasing hardnesses (tests referenced 1 to 5 in the tables below).

Two tablet formulae are produced with (about 10%) or without microalgal flour granules according to the invention, and the hardness and texture parameters are evaluated.

Tablets Containing Granules of Microalgal Biomass Flour

Formula:

| | | |
|---|---|---|
| PEARLITOL® Flash | 89.7% | 627.9 g |
| Batch 1 | 10.0% | 70.0 g |
| Bärlocher plant-based magnesium stearate | 0.3% | 2.1 g |

Procedure:
  Introduce all of the PEARLITOL® Flash and Batch 1 into a two-liter container, then mix for five minutes using a TURBULA® mixer.
  Add the magnesium stearate then mix again using the TURBULA® mixer for five minutes.
  Compress the mixture on a KORSCH XP1 tablet press equipped with flat punches of diameter 13 mm at a rate of 20 tablets/min.

TABLE 9

| | Tablets prepared according to five different compression forces | | | | |
|---|---|---|---|---|---|
| | 1 | 2 | 3 | 4 | 5 |
| Upper punch force (kN) | 5.033 | 10.025 | 15.376 | 20.056 | 25.470 |
| Standard deviation of upper punch (kN) | 0.026 | 0.053 | 0.088 | 0.145 | 0.126 |
| Lower punch force (kN) | 4.695 | 9.250 | 14.119 | 18.398 | 23.501 |
| Standard deviation of lower punch (kN) | 0.022 | 0.047 | 0.079 | 0.135 | 0.122 |
| Ejection force (N) | 96.777 | 201.465 | 258.040 | 299.089 | 306.315 |
| Standard deviation of ejection force (N) | 21.645 | 7.015 | 10.558 | 11.758 | 4.869 |
| Upper punch movement (mm) | 7.602 | 8.075 | 8.357 | 8.572 | 8.730 |
| Lower punch movement (mm) | 8.036 | 8.041 | 8.050 | 8.052 | 8.059 |
| Transmission (%) | 93.275 | 92.272 | 91.828 | 91.735 | 92.271 |
| Standard deviation of transmission (%) | 0.398 | 0.117 | 0.184 | 0.074 | 0.088 |
| Tablet weight (mg) | 601.2 | 600.8 | 602.6 | 602.0 | 604.9 |
| Standard deviation of weight (mg) | 0.8 | 1.0 | 1.0 | 1.6 | 1.0 |
| Tablet thickness (mm) | 4.45 | 4.05 | 3.84 | 3.67 | 3.59 |
| Standard deviation of thickness (mm) | 0.02 | 0.02 | 0.04 | 0.02 | 0.02 |
| Tablet density | 1.018 | 1.109 | 1.182 | 1.236 | 1.269 |
| Schleuniger hardness (N) | 0.0 | 23.2 | 54.5 | 81.5 | 106.9 |
| Standard deviation of hardness (N) | 0.0 | 0.8 | 1.4 | 1.0 | 2.3 |
| Tablet friability (%) | 100 | 100 | 0.22 | 0.16 | 0.11 |
| Complete disintegration time (s) | 138 | 148 | 147 | 156 | 158 |
| Standard deviation of disintegration (s) | 6 | 12 | 12 | 6 | 12 |

"Control" Tablets

Formula:

| | | |
|---|---|---|
| PEARLITOL® Flash batch E019F | 99.7% | 627.9 g |
| Bärlocher plant-based magnesium stearate | 0.3% | 2.1 g |

Procedure:
  Introduce the PEARLITOL® Flash and the magnesium stearate into a two-liter container and then mix using the TURBULA® mixer for five minutes.
  Compress the mixture on a KORSCH XP1 tablet press equipped with flat punches of diameter 13 mm at a rate of 20 tablets/min.

TABLE 10

| | Tablets prepared according to five different compression forces | | | | |
|---|---|---|---|---|---|
| | 1 | 2 | 3 | 4 | 5 |
| Upper punch force (kN) | 5.098 | 10.215 | 15.054 | 20.206 | 25.117 |
| Standard deviation of upper punch (kN) | 0.025 | 0.035 | 0.075 | 0.081 | 0.069 |
| Lower punch force (kN) | 4.845 | 9.600 | 14.109 | 18.918 | 23.550 |
| Standard deviation of lower punch (kN) | 0.024 | 0.030 | 0.061 | 0.070 | 0.058 |
| Ejection force (N) | 102.734 | 173.730 | 226.367 | 270.345 | 294.141 |
| Standard deviation of ejection force (N) | 3.316 | 10.527 | 10.472 | 13.976 | 9.736 |
| Upper punch movement (mm) | 7.864 | 8.293 | 8.561 | 8.732 | 8.894 |
| Lower punch movement (mm) | 8.255 | 8.217 | 8.207 | 8.188 | 8.189 |
| Transmission (%) | 95.036 | 93.978 | 93.724 | 93.629 | 93.760 |
| Tablet weight (mg) | 603.0 | 602.4 | 601.7 | 603.4 | 600.6 |
| Standard deviation of weight (mg) | 0.4 | 0.8 | 0.7 | 0.7 | 0.9 |
| Tablet thickness (mm) | 4.37 | 3.95 | 3.75 | 3.62 | 3.51 |
| Standard deviation of thickness (mm) | 0.01 | 0.01 | 0.01 | 0.02 | 0.01 |
| Tablet density | 1.040 | 1.149 | 1.206 | 1.256 | 1.289 |
| Schleuniger hardness (N) | 0.0 | 27.3 | 58.6 | 91.8 | 116.9 |
| Standard deviation of hardness (N) | 0.0 | 0.7 | 0.8 | 1.3 | 1.7 |
| Tablet friability (%) | 100 | 100 | 0.95 | 0.25 | 0.05 |
| Complete disintegration time (s) | 58 | 61 | 78 | 82 | 92 |
| Standard deviation of disintegration (s) | 6 | 4 | 7 | 8 | 9 |
| Standard deviation of transmission (%) | 0.325 | 0.276 | 0.165 | 0.099 | 0.092 |

Conclusions:
  Two different powders were compressed using the KORSCH alternating press equipped with flat punches of diameter 13 mm:
    As a control, a powder with PEARLITOL® Flash alone, another with 90% PEARLITOL® Flash and 10% of microalgal flour granules in accordance with the invention (Batch 1).
  The amount of lubricant is constant for the two formulae with 0.3% of magnesium stearate.
  On reading the results, it appears:
    that all the mixtures are homogeneous and flow perfectly. Likewise, there is no sticking and/or cleaving problem;
    that there is no negative influence of the "microalgal flour granules" component on the hardness of the tablets;
    that the microalgal flour granules according to the invention decrease the friability of the tablets.

Example 7

Formulation of the Granules of Microalgal Biomass Flour as Food Supplements

Eleven recipes were developed using the granules of Batch 1.

Leek Soup

| | Control | Test |
|---|---|---|
| Powdered whole milk | 33 | 33 |
| NUTRIOSE® FB06 | 8 | 8 |
| GLUCIDEX® IT21 | 7 | 7 |
| Chicken stock | 5 | 5 |

|  | Control | Test |
|---|---|---|
| Powdered leeks | 4 | 4 |
| PREGEFLO ® CH10 | 3 | 3 |
| Batch 1 | 0 | 1.5 |
| Powdered onions | 2.5 | 2.5 |
| Salt | 0.5 | 0.5 |
| Powdered garlic | 0.5 | 0.5 |
| Pepper | 0.1 | 0.1 |
| Dehydrated parsley | 0.3 | 0.3 |
| Total: | 63.9 | 65.4 |
| Water | 250 | 250 |

Premix all the powders together.
Disperse in hot water and mix.

Vegetable Soup (Glutamates)

| | |
|---|---|
| Powdered whole milk | 33 |
| NUTRIOSE ® FB06 | 8 |
| GLUCIDEX ® IT21 | 7 |
| Chicken stock | 2.5 |
| Powdered leeks | 0.5 |
| Powdered spinach | 3 |
| Powdered tomatoes | 1.5 |
| Powdered carrots | 1 |
| PREGEFLO ® CH10 | 3 |
| Batch 1 | 1.5 |
| Powdered onions | 1.4 |
| Roasted onions | 1.1 |

-continued

| | |
|---|---|
| Salt | 0.5 |
| Powdered garlic | 0.6 |
| Pepper | 0 |
| Glutamate | 0.2 |
| Nutmeg | 0.3 |
| Powdered parsley | 0.3 |
| Total: | 65.4 |
| Water | 250 |

Premix all the powders together.
Disperse in hot water and mix.

Fiber-Rich Lemon Cake

|  |  | Control | Test | Control | Test |
|---|---|---|---|---|---|
| A | Softened butter containing 82% fat | 200 | 200 | 19.31 | 19.31 |
|  | Caster sugar | 252 | 217 | 24.32 | 20.95 |
|  | Egg yolk colorant | 1 | 1 | 0.10 | 0.10 |
|  | Mane lemon flavoring | 0 | 4 | 0 | 0.39 |
|  | Vanilla flavoring | 4 | 0 | 0.39 | 0 |
|  | Salt | 3 | 3 | 0.29 | 0.29 |
| B | Whole egg | 180 | 180 | 17.37 | 17.37 |
|  | Semi-skimmed UHT milk | 100 | 100 | 9.65 | 9.65 |
| C | Leforest flour | 178 | 153 | 17.18 | 14.77 |
|  | Potato flour | 70 | 70 | 6.76 | 6.76 |
|  | W8024 pea fiber | 0 | 25 | 0 | 2.41 |
|  | NUTRIOSE ® FB06 | 0 | 35 | 0 | 3.38 |
|  | Spongolit 283 | 6 | 6 | 0.58 | 0.58 |
|  | Baking powder, volcano | 6 | 6 | 0.58 | 0.58 |
| D | Batch 1 | 0 | 36 | 0 | 3.47 |
|  | Chocolate chips | 36 | 0 | 3.47 | 0 |
|  | Total: | 1036 | 1036 | 100 | 100 |

In a hobart bowl using the sheet, mix A for 30 sec on speed 1 then 2 min on speed 2
Incorporate B, mix for 1 min on speed 1 then 2 min on speed 2
Add C, mix for 1 min on speed 1 then 3 min on speed 2
Incorporate D, mix for 15 sec on speed 1
Fill the molds and bake
Bake in a rotary oven for 18 min at 170° C.
Amount for 32 cakes of approximately 31 g
Water loss on baking: 15%
Batch 1 with 10% of NUTRIOSE® FB06

Cookies

|  |  | Control 100% sugar | Test 100% MALTISORB ® | Control 100% sugar | Test 100% MALTISORB ® |
|---|---|---|---|---|---|
| A | Water | 85 | 95 | 7.83 | 8.68 |
|  | Sodium bicarbonate | 3 | 3 | 0.28 | 0.27 |
|  | Ammonium bicarbonate | 2 | 2 | 0.18 | 0.18 |
| B | Confectioner's sugar | 180 | 0 | 16.59 | 0 |
|  | Maltisorb P200 | 0 | 180 | 0 | 16.44 |
| C | Fat, Biscuitine 500 | 160 | 160 | 14.75 | 14.61 |
|  | Soya lecithin | 2 | 2 | 0.18 | 0.18 |
| D | Leforest flour | 637 | 637 | 58.71 | 58.17 |
|  | Batch 1 | 10 | 10 | 0.92 | 0.91 |
|  | Salt | 2 | 2 | 0.18 | 0.18 |
|  | Vanilla flavoring | 4 | 4 | 0.37 | 0.37 |
|  | Total: | 1085 | 1095 | 100 | 100 |

In a hobart bowl using the sheet, mix A for 2 min on speed 1
Incorporate B, mix for 1 min on speed 1 then 2 min on speed 2
Add C, mix for 1 min on speed 1 then 3 min on speed 2
Introduce the mixture of powders C, mix for 4 min on speed 1
Leave the dough to stand for 15 minutes
Pass it through a rotary cookie machine
Place the cookies on a tray and bake

|  | Control | Test |
|---|---|---|
| Rotary oven 125° C. | 30 min | |
| Coloration | ++ | |
| Rotary oven 150° C. | 15 min | |
| Coloration | ++++ | |
| Rotary oven 170° C. | 9 min | |
| Coloration | ++++++ | 0 |

Ketchup

|  | Test 1 Without flavoring | Test 2 Ketchup flavoring | Test 3 Tomato flavoring | Test 4 Heinz flavoring | Test 5 Giv. tomato flavoring | Test 6 Ketchup flavoring + tomato flavoring (Mane) | Test 7 Heinz flavoring + Giv. tomato flavoring |
|---|---|---|---|---|---|---|---|
| Pea starch | 5 | 5 | 5 | 5 | 5 | 5 | 5 |
| CLEARAM ® CH2020 | 25 | 25 | 25 | 25 | 25 | 25 | 25 |
| MALTISORB ® 75/75 | 66 | 66 | 66 | 66 | 66 | 66 | 66 |
| NUTRIOSE ® FB17 | 60 | 60 | 60 | 60 | 60 | 60 | 60 |
| Vinegar 8° | 50 | 50 | 50 | 50 | 50 | 50 | 50 |
| Salt | 10 | 10 | 10 | 10 | 10 | 10 | 10 |
| Water | 281 | 281 | 280 | 281 | 275 | 281 | 278 |
| Mane ketchup flavoring | 0 | 0.25 | 0 | 0 | 0 | 0.125 | 0 |
| Mane tomato flavoring | 0 | 0 | 0.75 | 0 | 0 | 0.375 | 0 |
| Heinz ketchup flavoring | 0 | 0 | 0 | 0.35 | 0 | 0 | 0.175 |
| Givaudan tomato flavoring | 0 | 0 | 0 | 0 | 6 | 0 | 3 |
| Batch 1 | 2.5 | 2.5 | 2.5 | 2.5 | 2.5 | 2.5 | 2.5 |
| Acesulfame K | 0.3 | 0.25 | 0.25 | 0.25 | 0.25 | 0.25 | 0.25 |
| Total: | 499.8 | 500 | 499.5 | 500.1 | 499.75 | 500.25 | 499.925 |

Mix all the ingredients together
Cook in a water bath for 10 min at 90-95° C.

|  | Test 1 Without flavoring | Test 2 Ketchup flavoring | Test 3 Tomato flavoring | Test 4 Heinz flavoring | Test 5 Giv. tomato flavoring | Test 6 Ketchup flavoring + tomato flavoring (Mane) | Test 7 Heinz flavoring + Giv. tomato flavoring |
|---|---|---|---|---|---|---|---|
| Pea starch | 1.00 | 1.00 | 1.00 | 1.00 | 1.00 | 1.00 | 1.00 |
| CLEARAM ® CH2020 | 5.00 | 5.00 | 5.01 | 5.00 | 5.00 | 5.00 | 5.00 |
| MALTISORB ® 75/75 | 13.21 | 13.20 | 13.21 | 13.20 | 13.21 | 13.19 | 13.20 |
| NUTRIOSE ® FB17 | 12.00 | 12.00 | 12.01 | 12.00 | 12.01 | 11.99 | 12.00 |
| Vinegar 8° | 10.00 | 10.00 | 10.01 | 10.00 | 10.01 | 10.00 | 10.00 |
| Salt | 2.00 | 2.00 | 2.00 | 2.00 | 2.00 | 2.00 | 2.00 |
| Water | 56.22 | 56.20 | 56.06 | 56.19 | 55.03 | 56.17 | 55.61 |
| Mane ketchup flavoring | 0 | 0.05 | 0 | 0 | 0 | 0.02 | 0 |
| Mane tomato flavoring | 0 | 0 | 0.15 | 0 | 0 | 0.07 | 0 |
| Heinz ketchup flavoring | 0 | 0 | 0 | 0.07 | 0 | 0 | 0.04 |
| Givaudan tomato flavoring | 0 | 0 | 0 | 0 | 1.20 | 0 | 0.60 |
| Batch 1 | 0.50 | 0.50 | 0.50 | 0.50 | 0.50 | 0.50 | 0.50 |
| Acesulfame K | 0.06 | 0.05 | 0.05 | 0.05 | 0.05 | 0.05 | 0.05 |
| Total: | 100 | 100 | 100 | 100 | 100 | 100 | 100 |

Mayonnaise

|  |  | Control | Test | Control | Test |
|---|---|---|---|---|---|
| A | Caster sugar | 50 | 50 | 5.00 | 4.98 |
|  | Vinegar 8° | 100 | 100 | 10.00 | 9.95 |
|  | Mustard | 40 | 40 | 4.00 | 3.98 |
|  | Salt | 30 | 30 | 3.00 | 2.99 |
|  | Water | 393 | 393 | 39.30 | 39.10 |
|  | Egg yolk colorant | 1.5 | 1.5 | 0.15 | 0.15 |
|  | Batch 1 | 0 | 5 | 0 | 0.50 |
|  | Potassium sorbate (E202) | 0.5 | 0.5 | 0.05 | 0.05 |
| B | Fresh egg yolk | 50 | 50 | 5.00 | 4.98 |
| C | Rapeseed oil | 300 | 300 | 30.00 | 29.85 |
|  | PREGEFLO ® PJ30 | 35 | 35 | 3.50 | 3.48 |
|  | Total: | 1000 | 1005 | 100 | 100 |

In a mixer bowl, mix A for 1 min
Incorporate the egg yolk (B)
Trickle in C, mix at maximum speed
Continue the stirring for 1 minute Wine Gums

|  | Test |
|---|---|
| FLOKYS ® B6080S | 45.5 |
| CLEARGUM ® LG7015 | 10.8 |
| Pectin PG769S | 0.5 |
| Sucrose | 26.3 |
| Batch 1 | 1.0 |
| Water | 14.2 |
| 50% citric acid | 2.8 |
| Total: | 101.0 |

Coated Peanuts

|  | Test |
|---|---|
| Peanuts | 27.3 |
| Nutriose FB 06 | 34.4 |
| Batch 1 | 3 |

-continued

|  | Test |
|---|---|
| PREGEFLO ® CH10G | 25.3 |
| Flour | 6.2 |
| Corn starch | 3.8 |
| Total: | 100 |

Heat the NUTRIOSE® FB 06 syrup (40% solids) at 50° C. in a water bath

Mix the powders

Place the roasted peanuts in the turbine

Add the NUTRIOSE® FB 06 syrup (15-20 g) and the mixture of powders (approximately 30 g)

Repeat this operation as many times as possible

Bake in an oven at 200° C. for 7 minutes

Pesto Sauce

|  | Control | Test 1 | Test 2 |
|---|---|---|---|
| Basil | 33.0 | 24.0 | 20.0 |
| Cheese | 5.2 | 7.2 | 5.0 |
| Salt | 1.5 | 1.5 | 1.5 |
| Lactic acid | 0.7 | 0 | 0 |
| Pine nuts | 2.1 | 2.1 | 0.5 |
| Garlic | 2.0 | 2.0 | 0.3 |
| Potassium sorbate | 0 | 0.7 | 0.1 |
| Batch 1 | 0 | 1.0 | 4.0 |
| Sunflower oil | 40.0 | 40.0 | 30.0 |

-continued

|  | Control | Test 1 | Test 2 |
|---|---|---|---|
| PGHV starch | 1.0 | 4.0 | 1.0 |
| Glucose syrup | 8.0 | 8.0 | 1.5 |
| Olive oil | 1.5 | 3.0 | 0 |
| PREGEFLO ® CH20 | 0 | 0 | 2.0 |
| Water | 0 | 6.5 | 34.1 |
| Total: | 95 | 100 | 100 |

Dry Dog Food

|  | Initial recipe | 1% chlorella | 3% chlorella | 5% chlorella |
|---|---|---|---|---|
| Poultry meal | 83.5 | 82.5 | 80.5 | 78.5 |
| Poultry fat | 3.5 | 3.5 | 3.5 | 3.5 |
| Sucrose | 5.0 | 5.0 | 5.0 | 5.0 |
| Salt | 1.0 | 1.0 | 1.0 | 1.0 |
| Batch 1 | 0 | 1 | 3 | 5 |
| Water | 7 | 7 | 7 | 7 |
| Total: | 100.0 | 100.0 | 100.0 | 100.0 |
| Vit B12/meal (Beagle) (for 240 g) | 0.0 | 2.4 | 7.2 | 12.0 |
| Vit B12/meal (Labrador) (for 500 g) | 0.0 | 5.0 | 15.0 | 25.0 |

Mixing of the powders+fat

Extrusion with provision of water sufficient for cooking the dry food

Cooking T° C.: 115-130° C.

~240 g of dry food for dogs of 10 to 12 kg of Beagle type

~500 g of dry food for dogs of ~40 kg of Labrador type

Vegetable Croquettes

|  | Initial recipe | Chlorella | Chlorella | Chlorella | Chlorella | Steak (100 g) |
|---|---|---|---|---|---|---|
| NUTRALYS ® F85G TVP | 17.0 | 17.0 | 17.0 | 17.0 | 17.0 | 17.0 |
| Water | 74.5 | 72.2 | 72.2 | 71.2 | 69.9 | 70.8 |
| Albumen | 3.7 | 3.7 | 3.7 | 3.7 | 3.7 | 3.7 |
| Pregeflo MI20A | 2.0 | 2.0 | 2.0 | 2.0 | 2.0 | 2.0 |
| Chicken flavoring | 2.5 | 0 | 0 | 0 | 0 | 0 |
| Powdered onions | 0 | 0.60 | 0.60 | 0.60 | 0.60 | 0.60 |
| Salt | 0.3 | 0 | 0 | 0 | 0 | 0 |
| Batch 1 | 0 | 0.5 | 1 | 2 | 3.3 | 2.0 |
| Powdered carrot | 0 | 0 | 0 | 0 | 0 | 0 |
| Powdered tomato | 0 | 0 | 0 | 0 | 0 | 0 |
| Powdered spinach | 0 | 4.0 | 3.5 | 3.5 | 3.5 | 3.5 |
| Powdered parsley | 0 | 0 | 0 | 0 | 0 | 0.3 |
| Nutmeg | 0 | 0 | 0 | 0 | 0 | 0.1 |
| Colorant | 0 | 0 | 0 | 0 | 0 | 0 |
| Total: | 100.0 | 100.0 | 100.0 | 100.0 | 100.0 | 100.0 |
| Vit B12/meal (60 or 100 g) | 0.0 | 0.3 | 0.6 | 1.2 | 2.0 | 2.0 |
| Daily intake | 0% | 15% | 30% | 60% | 99% | 100% |

| Batter: |
| --- |
| 43.5% pea starch; |
| 1.2% PREGEFLO ® CH2020; |
| 1.5% salt; |
| 53.8% water |

Prepare a vegetable stock: 1 cube in 300 ml of boiling water

Hydrate the Nutralys 98% TVP (70 g) in this stock for 30 min

Cut in a blender (1 min, twice) so as to obtain a fibrous appearance

Add the mixture of powders

Shape the croquettes (10 g) and cook in a steam oven for 30 min

Deep freeze

Immerse the croquettes in the batter, then in the breadcrumbs

Fry at 190° C. for 1 min

Deep freeze

Cook the nuggets by frying at 190° C. for 3 min 30

It is considered that the meal is composed of six "croquettes" of 10 g. The recommended daily VitB12 intake is 2 g (minimum)

Table 11 below presents the results of these conditions for incorporating the microalgal flour granules in accordance with the invention as food supplements, compared with their functional properties.

TABLE 11

| | | Dose of granules of microalgal biomass flour (Batch 1) | | | | |
| --- | --- | --- | --- | --- | --- | --- |
| | | In g | | In % | | |
| Applications | Target | Per portion | For 100 g | Per portion | For 100 g | Advantages |
| Leek soup | nutrition | 1.5 | 0.5 | 0.5 | 0.5 | easier dispersion, better distribution |
| Vegetable soup (glutamate) | nutrition | 0.2 | 0.1 | 0.06 | 0.1 | easier dispersion, better distribution |
| Cake | nutrition decoration | 0.97 | 3.1 | 3.1 | 3.1 | milling to obtain 100% *chlorella* granules for speckled cake |
| Cookies | nutrition | | 0.9 | | 0.9 | coarse milling to obtain 100% microalgal biomass granules for speckled cake |
| Ketchup | colorant | | 0.5 | | 0.5 | neutral |
| Mayonnaise | colorant | | 0.5 | | 0.5 | neutral |
| Wine gums | nutrition colorant | | 1 | | 1 | easier dispersion of the product in a viscous mass |
| Coated peanuts | colorant | | 3 | | 3 | mixing of powders and distribution facilitated |
| Pesto sauce | colorant | | 1 | | 1 | neutral |
| Vegetable croquettes (2%) | colorant | 1.2 | 2 | 1.2 | 2 | neutral |
| Dry dog food | nutrition | | | | 15 | facilitates extruder feeding |

Good results were obtained by incorporating the granules of microalgal biomass flour according to the invention into recipes for:

breakfast cereals,
yogurts,
seasoning flakes,
cream dessert (pistachio),
dry food for alevins,
dry horse food.

Example 8

Formulation of the Granules of Microalgal Biomass Flour as Food Supplements

Ten recipes similar to those of example 7 were developed using the granules of Batch 3.

Cookies (Conventional Recipe and Recipe with Cereals)

| | Control conventional recipe | Batch 3 conventional recipe | Control cereal recipe | Batch 3 cereal recipe |
| --- | --- | --- | --- | --- |
| Water | 60 | 60 | 65 | 65 |
| Sodium bicarbonate | 3 | 3 | 3.5 | 3.5 |
| Ammonium bicarbonate | 2 | 2 | 1.5 | 1.5 |
| Sucrose | 180 | 180 | 150 | 150 |
| Honey | 0 | 0 | 25 | 25 |
| Glucose syrup 4779 | 25 | 25 | 0 | 0 |
| Fat, Biscuitine | 130 | 130 | 150 | 150 |

|  | Control conventional recipe | Batch 3 conventional recipe | Control cereal recipe | Batch 3 cereal recipe |
|---|---|---|---|---|
| 500 |  |  |  |  |
| Soya lecithin | 2 | 2 | 2 | 2 |
| Wheat flour | 576 | 466 | 435 | 330 |
| Wholewheat flour | 0 | 0 | 65 | 64 |
| Oat flakes | 0 | 0 | 80 | 80 |
| Batch 3 | 0 | 110 | 0 | 105 |
| Skimmed milk powder | 15 | 15 | 15 | 15 |
| Salt | 2 | 2 | 2 | 2 |
| Sodium pyrophosphate | 2 | 2 | 3 | 3 |
| Vanilla flavoring | 2 | 2 | 2 | 2 |
| Butter flavoring M_0056299 | 1 | 1 | 1 | 2 |
|  | 1000 | 1000 | 1000 | 1000 |

Breads

|  | Control | NUTRALYS® Pea-BF | Batch 3 + NUTRALYS® Pea-BF | Batch 3 |
|---|---|---|---|---|
| Wheat flour | 970 | 860 | 860 | 860 |
| Gluten | 30 | 40 | 40 | 40 |
| Batch 3 | 0 | 0 | 40 | 100 |
| NUTRALYS® pea based (BF) | 0 | 100 | 60 | 0 |
| Salt | 18 | 18 | 18 | 18 |
| Dry yeasts | 7 | 7 | 7 | 7 |
| Ascorbic acid | 0.2 | 0.2 | 0.2 | 0.2 |
| NUTRILIFE® AM17, enzyme | 0.2 | 0.2 | 0.2 | 0.2 |
| Water (20° C.) | 600 | 725 | 725 | 700 |
|  | 1625.4 | 1750.4 | 1750.4 | 1725.4 |

Breakfast Cereals

| % | Control | Nutralys pea protein + Batch 3 |
|---|---|---|
| Wholewheat flour | 47.6 | 39.9 |
| Corn meal | 10.5 | 5.6 |
| Corn starch | 8.4 | 4.2 |
| NUTRALYS® W wheat protein | 0.0 | 12.0 |
| Batch 3 | — | 5.5 |
| Sucrose | 15.5 | 15.5 |
| Glucose syrup 7080 | 15.0 | 15.0 |
| Water | 3.0 | 3.0 |
|  | 100.0 | 100.0 |

Pumpkin Velouté

| In % | Control % | NUTRALYS® S85F % | Batch 3 % | NUTRALYS® S85F + Batch 3 % | NUTRALYS® S85F + Batch 3 % |
|---|---|---|---|---|---|
| Water | 53.25 | 52.15 | 51.75 | 52.00 | 50.25 |
| Potatoes | 2 | 2 | 2 | 2.00 | 2.00 |
| Carrots | 8 | 8 | 8 | 8.00 | 8.00 |
| Pumpkin | 23.5 | 23.5 | 23.5 | 23.50 | 23.50 |
| Thinly sliced onions | 3 | 3 | 3 | 3.00 | 3.00 |
| Leeks | 3 | 3 | 3 | 3.00 | 3.00 |
| Cream (35% fat) | 2.6 | 2.6 | 2.6 | 2.60 | 2.60 |
| CLEARAM® CH2020 | 0.8 | 0.8 | 0.8 | 0.80 | 0.80 |
| Sugar | 1 | 1 | 1 | 1.00 | 1.00 |
| Butter (82% fat) | 1.1 | 1.1 | 1.1 | 1.10 | 1.10 |
| Salt | 0.7 | 0.7 | 0.7 | 0.70 | 0.70 |
| I50M pea fibers | 0.8 | 0.8 | 0.8 | 0.80 | 0.80 |
| Yeast extract | 0.2 | 0.2 | 0.2 | 0.20 | 0.20 |

| In % | Control % | NUTRALYS® S85F % | Batch 3 % | NUTRALYS® S85F + Batch 3 % | NUTRALYS® S85F + Batch 3 % |
|---|---|---|---|---|---|
| Batch 3 | — | — | 1.5 | — | — |
| NUTRALYS® S85F pea protein | — | 1.1 | — | — | — |
| Mixture of 60% NUTRALYS® S85F pea protein/ 40% Batch 3 | 0 | — | — | 1.25 | 3.00 |
| Nutmeg | 0.05 | 0.05 | 0.05 | 0.05 | 0.05 |
| | 100 | 100 | 100 | 100 | 100.00 |

Leek/Potato Velouté

| In % | Control % | NUTRALYS® S85F + Batch 3 % | NUTRALYS® S85F + Batch 3 % |
|---|---|---|---|
| Water | 50.6 | 49.9 | 48.25 |
| Potatoes | 14.5 | 14.5 | 14.5 |
| Spinach | 5.5 | 5.5 | 5.5 |
| Thinly sliced onions | 4.4 | 4.4 | 4.4 |
| Leeks | 18.0 | 18.0 | 18 |
| Cream (35% fat) | 2.2 | 2.2 | 2.2 |
| CLEARAM® CH2020 | 0.8 | 0.8 | 0.6 |
| Sugar | 1.0 | 1.0 | 1 |
| Butter (82% fat) | 1.5 | 1.5 | 1.5 |
| Salt | 0.7 | 0.7 | 0.8 |
| I50M pea fibers | 0.8 | 0.8 | 0.8 |
| Mixture of 60% NUTRALYS S85F pea protein/40% Batch 3 | 0.0 | 0.7 | 2.45 |
| | 100 | 100 | 100 |

Mix for Drinks Containing 21% Proteins

| In % | Control % | Batch 3 % | NUTRALYS® S85F + Batch 3 % |
|---|---|---|---|
| Skimmed milk powder | 28.5 | 30.2 | 28.6 |
| Sugar | 27.0 | 27.0 | 27.0 |
| GLUCIDEX® IT 47 | 23.5 | 20.3 | 22.4 |
| Cocoa powder (23-24% fat) | 6.0 | 6.0 | 6.0 |
| NUTRALYS® XF | 4.0 | 0.0 | 5.4 |
| NUTRALYS® WF | 4.0 | 0.0 | 0.0 |
| Batch 3 | 0.0 | 9.5 | 3.6 |
| WPC 90 | 4.0 | 4.0 | 4.0 |
| Pregeflo® C100 | 3.0 | 3.0 | 3.0 |
| Total | 100.0 | 100.0 | 100.0 |

Mix for Chocolate Cream

| | | NUTRALYS® XF (60%)/ Batch 3 (40%) ratio | |
|---|---|---|---|
| In % | Control % | B-milk protein isolate substitution % | C-whole milk powder substitution % |
| Milk protein isolate (Prodiet 85_Ingredia) | 36.5 | 0.00 | 36.5 |
| NUTRALYS® XF_Lab 4460 (W106R) | 0.00 | 24.50 | 6.00 |
| HPAF (EA342) | 0.00 | 16.30 | 4.00 |
| Whole milk powder | 27.00 | 27.00 | 0.00 |
| "Low fat" cocoa powder | 13.00 | 13.00 | 13.00 |
| GLUCIDEX® IT19 | 0.00 | 0.00 | 17.00 |
| PREGEFLO® C100 | 5.00 | 3.00 | 5.00 |
| NUTRIOSE® FM06 | 6.00 | 3.70 | 6.00 |
| Caramel colorant (M_0052208) | 2.00 | 2.00 | 2.00 |
| Carrageenans (Matgum L03_AGI) | 3.70 | 3.70 | 3.70 |
| Guar gum (Matguar 5000_AGI) | 1.11 | 1.11 | 1.11 |
| Xanthan gum (F80_AGI) | 1.11 | 1.11 | 1.11 |
| Salt | 1.50 | 1.50 | 1.50 |
| Aspartame | 0.40 | 0.40 | 0.40 |
| Potassium acesulfame | 0.20 | 0.20 | 0.20 |
| Mix of vitamins PNU CN 02_VitaBlend | 0.12 | 0.12 | 0.12 |
| Mix of minerals PNU CN 02_VitaBlend | 2.36 | 2.36 | 2.36 |
| Total | 100.00 | 100.00 | 100.00 |

100% Vegetable-based Drink

| In % | Batch 3 % |
|---|---|
| NUTRALYS® S85F pea protein | 2.81 |
| Lipid-rich *chlorella* biomass | 1.70 |
| Batch 3 | 1.87 |
| SYMRISE 688571 masking flavor | 0.187 |
| SYMRISE 320982 pear flavor | 0.204 |
| SYMRISE 826892 vanilla flavoring | 0.041 |
| CLEARGUM® CK2020 | 0.26 |
| Sugar cane | 3.40 |
| Water | 89.53 |
| | 100 |

Table 12 below presents the results of these conditions for incorporating the microalgal flour granules in accordance with the invention as food supplements, compared with their functional properties.

TABLE 12

| Application | Targets | Lightening | % total proteins | % protein-rich algal flour | Other proteins used in the formula | Advantages |
|---|---|---|---|---|---|---|
| BREAD-MAKING PRODUCTS | Conventional cookie | source | 14.1 | 11 | wheat | No modification of the recipe, the process or the baking time. Cookie texture unmodified, taste correct |
| | Cereal cookie | source | 14.3 | 10.5 | wheat | No modification of the recipe, the process or the baking time. Cookie texture unmodified, taste correct |
| | Bread | rich | | 5.7 | wheat | No recipe modification, no process modification, doughs similar to the control. |
| | | | | 2.3 | wheat, pea | No major influence on bread texture, coloration slightly stronger. |
| | Breakfast cereals | rich | 19.3 | 5.5 | pea | ok in terms of taste and crunchiness |
| SOUPS | Pumpkin velouté | source | 1.4 | 0.5 | pea | The protein-enriched soup formulae give better results using a mix of 60% of Nutralys ® S85F/40% batch 3, in relation to both texture and taste. This 60/40 ratio is all the more advantageous since it makes it possible to optimize the amino acid profile (notion of PDCAAS). Batch 3 and the NUTRALYS ® S85F withstand the heat treatment |
| | | rich | 2.6 | 1.2 | pea | |
| | Leek-potato velouté | source | 1.5 | 0.3 | pea | |
| | | rich | 2.8 | 1 | pea | |
| NUTRITION | Mix for drink containing 21% proteins | | 21.5 | 3.6 | whey, pea skimmed milk | Good consistency and body; taste ok |
| | Mix for chocolate cream | | 39.9 | 4 | isolated milk, pea | Good texture and acceptable taste |
| | Algal flour-based 100% vegetable drink | | 3.51 | 1.87 | pea | Mixture of flour rich in lipids and proteins and of NUTRALYS ® |

Example 9

Incorporation of the Granules of Microalgal Biomass Flour into High-protein Bars In this example, high-protein bars are produced which combine the *Chlorella protothecoides* biomass flour granules (Batch 3 of example 5) with other ingredients sold by the applicant company, according to the recipes presented in the table below.

High-protein Bars

| In % | Control % | Batch 3 % | 60/40 NUTRALYS ® XF + BF/Batch 3 % |
|---|---|---|---|
| FLOLYS ® E7081S | 21.10 | 21.10 | 20.25 |
| Fat | 3.00 | 3.00 | 2.90 |
| Batch 3 | — | 37.44 | 16.10 |
| Cocoa powder | 0.90 | 0.90 | 0.90 |
| Chocolate maltitol | 15.00 | — | — |
| NEOSORB ® 70/70 | 1.75 | 1.75 | 1.68 |
| NUTRALYS ® XF + BF | 21.40 | — | 14.64 |
| NUTRALYS ® WF | 15.20 | — | 9.98 |
| Chocolate sugar | 0.00 | 15.00 | 15.00 |
| NUTROISE ® 06 | 7.20 | 7.20 | 7.24 |
| Water | 12.80 | 12.80 | 10.17 |
| Total | 98.35 | 99.19 | 98.86 |

Conclusions:

The formation of a flexible dough is very rapidly observed during kneading; and during the incorporation of wheat and pea proteins, the texture is described as flexible, chewable and non-granular. The "roasted cereals" taste is judged to be pleasant.

Example 10

Incorporation of the Granules of Microalgal Biomass Flour into Sports Drinks In this example, high-protein drinks for sports people are produced which combine the *Chlorella protothecoides* biomass flour granules (Batch 3 of example 5) with other ingredients sold by the applicant company, according to the recipes presented in the table below.

Mix for Drinks Containing 74% Proteins

| In % | Control % | Batch 3 % | NUTRALYS ® S85F + Batch 3 % |
|---|---|---|---|
| Whey protein isolate WPC 80 | 49.62 | 69.46 | 49.62 |
| NUTRALYS ® XF | 49.62 | — | 29.77 |
| Batch 3 | — | 29.78 | 19.85 |
| REBAUDIOSIDE A (Stevia) | 0.06 | 0.06 | 0.06 |
| MANE vanilla flavoring M555943 | 0.70 | 0.7 | 0.7 |
| | 100 | 100 | 100 |

Conclusions:

The formulae are very suitable; while the taste remains vegetable, there is no bitterness. The *Chlorella protothecoides* biomass flour even confers a pleasant fullness in the mouth.

The invention claimed is:

1. Granules of microalgal biomass flour, the granules comprising:

a particle size distribution, measured on an LS laser particle size analyzer of the COULTER® brand, having a Dmode of between 60 and 300 µm and a D4,3 between 70 and 420 µm, a bulk density, measured on a HOSOKAWA Powder Characteristics Tester, of between 0.6 g/ml and 0.7 g/ml, a compressibility, measured on a HOSOKAWA Powder Characteristics Tester, of between 15% and 25%, said microalgal biomass comprising at least 50% protein by dry weight.

2. The granules as claimed in claim 1, wherein the microalga is chosen from the group consisting of *Chlorella sorokiniana* and *Chlorella protothecoides*.

3. The granules as claimed in claim 2, wherein the microalga is *Chlorella sorokiniana*.

4. The granules as claimed in claim 2, wherein the microalga is *Chlorella protothecoides*.

5. The granules as claimed in claim 3, which have a particle size distribution having a Dmode of between 70 and 130 µm and a D4,3 between 75 and 140 µm.

6. The granules as claimed in claim 4, which have a particle size distribution having a Dmode of between 200 and 280 µm and a D4,3 between 300 and 420 µm.

7. The granules as claimed in claim 1, wherein the granules further comprise a degree of wettability, the degree of wettability measured according to a Test B, by the height of the product decanted in a beaker, at a value of between 5 and 25 mm.

8. The granules as claimed in claim 3, wherein the granules further comprise a degree of wettability, the degree of wettability measured according to a Test B, by the height of the product decanted in a beaker, at a value of between 5 and 15 mm.

9. The granules as claimed in claim 3, wherein the granules further comprise a degree of wettability, the degree of wettability measured according to a Test B, by the height of the product decanted in a beaker, at a value of between 15 and 25 mm.

10. The granules as claimed in claim 1, wherein the granules further comprise a specific surface area, the specific surface area measured according to a BET method, of between 0.45 and 0.70 $m^2/g$.

11. The granules as claimed in claim 3, wherein the granules further comprise a specific surface area, the specific surface area measured according to a BET method, of between 0.45 and 0.50 $m^2/g$.

12. The granules as claimed in claim 4, wherein the granules further comprise a specific surface area, the specific area measured according to a BET method, of between 0.60 and 0.70 $m^2/g$.

13. A process for preparing the granules as claimed in claim 1, the method comprising the steps of:
1) preparing a suspension of microalgal biomass in water at a solids content of between 10% and 35% by dry weight,
2) spraying the suspension in a vertical spray-drier equipped with a moving belt at its base, and with a high-pressure nozzle in its upper part, while regulating:
   the first temperature of the primary air at a value of between 160 and 220° C.,
   the second temperature of the primary air at a value of between 90 and 150° C.,
   the spray pressure at a value of between 50 and 250 bar,
3) regulating the entry temperature of the post-drying zone on the moving belt at a value of between 70 and 90° C., and regulating the temperature of the cooling zone at a value of between 15 and 25° C.,
4) collecting the granules of microalgal biomass flour thus obtained.

14. A product selected from food for human consumption, animal feed, pharmaceuticals and cosmetics, comprising the granules according to claim 1.

15. The product as claimed in claim 14, in the form of orodispersible tablets.

16. The product as claimed in claim 14, which is in the form of soups, sauces, cakes, cookies, breakfast cereals, mayonnaise, ketchup, wine gums, coated peanuts, yogurts, cream desserts, vegetable nuggets, or seasoning flakes.

17. The product as claimed in claim 14, which is in the form of a bar.

18. The product as claimed in claim 14, which is in the form of a sports drink.

19. The product as claimed in claim 14, selected from the group consisting of dry dog food, dry food for horses, or dry food for alevins.

20. The granules of claim 1, wherein the compressibility, measured on a HOSOKAWA Powder Characteristics Tester is between 18% and 21%.

21. The method of claim 13, wherein the spray pressure is at a value of between 80 and 150 bar.

* * * * *